United States Patent [19]

Staerz

[11] Patent Number: 6,060,054
[45] Date of Patent: *May 9, 2000

[54] PRODUCT FOR T LYMPHOCYTE IMMUNOSUPPRESSION

[75] Inventor: Uwe D. Staerz, Denver, Colo.

[73] Assignee: National Jewish Medical and Research Center, Denver, Colo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/630,172

[22] Filed: Apr. 10, 1996

[51] Int. Cl.[7] .......................... A61K 39/395; A61K 38/17; C12N 15/12; C12N 15/13
[52] U.S. Cl. ...................................... 424/134.1; 424/192.1; 424/193.1; 435/69.1; 435/455; 435/471; 530/350; 530/387.3; 530/391.1; 514/8; 514/885
[58] Field of Search .............................. 424/130.1, 134.1, 424/192.1, 194.1, 193.1, 195.4; 435/69.1, 70.1, 71.1, 172.3, 251.3, 455, 471; 514/8, 885; 530/387.3, 391.1, 350

[56] References Cited

U.S. PATENT DOCUMENTS

| | | |
|---|---|---|
| 4,950,480 | 8/1990 | Barber et al. . |
| 5,098,833 | 3/1992 | Lasky et al. ............................ 435/69.1 |
| 5,116,964 | 5/1992 | Capon et al. ............................. 536/27 |
| 5,204,449 | 4/1993 | Puri ...................................... 530/391.7 |
| 5,225,538 | 7/1993 | Capon et al. .......................... 530/387.3 |
| 5,242,687 | 9/1993 | Tykocinski et al. . |
| 5,336,603 | 8/1994 | Capon et al. ........................... 435/69.7 |
| 5,359,046 | 10/1994 | Capon et al. ........................... 536/23.4 |
| 5,428,130 | 6/1995 | Capon et al. ............................ 530/350 |

FOREIGN PATENT DOCUMENTS

| | | |
|---|---|---|
| WO 90/08187 | 7/1990 | WIPO . |
| WO 90/10385 | 9/1990 | WIPO . |

OTHER PUBLICATIONS

Rouleau et al. J. Immunol. 151: 3547–3556 (1993).
Gross et al. Faseb J. 6: 3370–3378 (1992).
Rabin et al. Cell. Immunol. 149: 24–38 (1993).
ATCC Cell Lines and Hybridomas 8th Editon 1994 Rockville MD 1994 p. 402 Only.

*Primary Examiner*—Christina Y. Chan
*Assistant Examiner*—Phillip Gambel
*Attorney, Agent, or Firm*—Sheridan Ross P.C.

[57] ABSTRACT

The present invention relates to a product and process for suppressing an immune response using a T lymphocyte immunosuppression molecule capable of blocking cell surface molecules responsible for T cell activation. Disclosed is a CD4 or CD2 molecule, associated with an immunoglobulin molecule capable of binding to a major histocompatibility antigen. Also disclosed is a method to produce a T lymphocyte molecule, a therapeutic composition comprising a T lymphocyte immunosuppression molecule and methods to use T lymphocyte immunosuppression molecules in therapeutic processes requiring suppression of an immune response.

31 Claims, 2 Drawing Sheets

C57BL/6@Balb/c
50,000 responders

C57BL/6@Balb/c
200,000 responders

Balb/c@C57BL/6
50,000 responders

Balb/c@C57BL/6
200,000 responders

PRODUCT FOR T LYMPHOCYTE IMMUNOSUPPRESSION

GOVERNMENT RIGHTS

This invention was made in part with government support under AI35194, awarded by the National Institutes of Health. The government has certain rights to this invention.

FIELD OF THE INVENTION

The present invention relates to a product and process for immunosuppression of subjects having undesired immunological reactivities and in subjects in need of cell, tissue or organ transplant survival. More particularly, the present invention relates to a T lymphocyte veto molecule (hereinafter defined) and the use of such a molecule as an immunoregulator to effect therapeutic objectives.

BACKGROUND OF THE INVENTION

A wide variety of medical treatments require regulation of the immune response in a patient. Such treatments include, for example, vaccinations, treatments for autoimmune diseases, immunodeficiency diseases, immunoproliferative diseases and treatments involving the transplantation of organs and skin. Traditional reagents and methods used to regulate a subject's immune response often results in unwanted side effects. For example, immunosuppressive reagents such as cyclosporin A, azathioprine and prednisone are used to suppress the immune system of a patient with an autoimmune disease or patients receiving transplants. Such reagents, however, suppress a patient's entire immune response, thereby crippling the ability of the patient to mount an immune response against infectious agents not involved in the original disease. Due to such harmful side effects and the medical importance of immune regulation, reagents and methods to regulate specific parts of the immune system have been the subject of study for many years.

Introduction of an antigen into a host initiates a series of events culminating in an immune response. In addition, self-antigens can result in immunological tolerance or activation of an immune response against self-antigens. A major portion of the immune response is regulated by the interaction of a stimulator cell (defined in detail below) with a responding cell (defined in detail below).

Particular reagents having immunoregulatory potential of cell to cell interactions have been suggested by various investigators. Tykocinski et al. disclose in U.S. Pat. No. 5,242,687, issued Sep. 7, 1993, a composition comprising a CD8 peptide associated with a secondary ligand, including an Fc domain of immunoglobulin or a major histocompatibility molecule (MHC). Tykocinski et al. do not teach or suggest such a composition involving CD4, CD2, CD28, CTLA4 or fas-ligand proteins which are known to have significantly different functions in various immunity mechanisms.

In U.S. Pat. No. 5,336,603, issued Aug. 9, 1994, Capon et al. disclose "immunoadhesons" useful for immunomodulatory therapy. Capon et al. disclose adhesons as cell surface polypeptides, examples of which include CD8, CD4 and CD2, that can be combined with an immunologically active non-adheson polypeptide. Capon et al., however, do not teach or suggest a T cell veto molecule useful for immunosuppression and particularly a molecule that prevents the specific activation of responding cells by stimulator cells to suppress an immune response.

As such, there remains a need for therapeutic reagents and strategies that suppress an immune response in a safe and effective manner.

SUMMARY

The present invention relates to a novel product and process for treatment of subjects in need of the abrogation of immunological reactivities. According to the present invention there are provided soluble or membrane-bound T lymphocyte veto molecules for immunosuppression in vivo or in vitro. The present invention overcomes traditional problems with immunoregulatory reagents by specifically regulating stimulator cell activation of responding cells capable of killing transplanted cells or capable of responding to autoantigens. This act of regulation is referred to herein as T cell veto. A molecule capable of T cell veto is referred to herein as a T cell veto molecule. In addition, the immunoregulatory reagents of the present invention can be administered locally, thereby alleviating problems that arise from extensive immunosuppression in an animal.

More specifically, one embodiment of the present invention includes a T lymphocyte veto molecule which includes a chimeric molecule having a protein selected from the group consisting of CD4 protein, CD2 protein, CD28 protein, CTLA4 protein, Fas-ligand protein, CD5 protein, CD7 protein, CD9 protein, CD11 protein, CD18 protein, CD27 protein, CD43 protein, CD45 protein, CD48 protein, B7.1 protein and B7.2 protein. The protein is linked to a targeting polypeptide that binds to a molecule that differentiates a host cell from a tissue graft cell. A further embodiment of the present invention is a T lymphocyte veto molecule which includes a chimeric molecule having one of such proteins. In this embodiment, the protein is linked to a targeting polypeptide that binds to a molecule which selectively targets a stimulator cell involved in an autoimmune response. In further aspects of these embodiments, the targeting polypeptide can be an immunoglobulin molecule, a growth factor or a tissue specific antigen. Such T lymphocyte veto molecules can be included in therapeutic compositions which also include pharmaceutically acceptable carriers.

A further embodiment of the present invention includes a recombinant cell, which has a first recombinant molecule having a nucleic acid molecule operatively linked to an expression vector, wherein the nucleic acid molecule has a sequence which encodes one of the proteins mentioned above. The recombinant cell further includes a second recombinant molecule having a nucleic acid molecule operatively linked to an expression vector wherein the nucleic acid molecule encodes a protein which is a targeting molecule that differentiates between a host cell and a tissue graft cell.

A further aspect of the present invention includes a method for producing a T lymphocyte veto molecule. This method includes providing a first protein as mentioned above, providing a second protein which is a targeting molecule that differentiates a host cell from a tissue graft cell, and linking the first protein to the second protein to form a chimeric molecule.

The present invention also includes a method to suppress an immune response which includes exposing chimeric molecules of the present invention to a stimulator cell that can interact specifically with the chimeric molecule under conditions for reduction of an immune response.

A further aspect of the present invention is a method to alleviate tissue transplant rejection. This method includes administering to an animal an effective amount of a therapeutic composition which includes a T lymphocyte veto molecule of the present invention.

DETAILED DESCRIPTION OF THE INVENTION

Figure 1A:
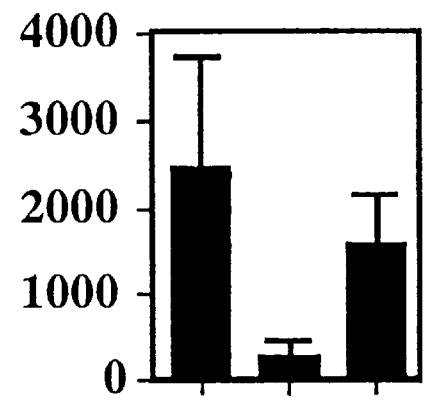
FIGS. 1A–1D shows the results of an experiment in which a T lymphocyte veto molecule is capable of specifically inhibiting the proliferation of CD4+ responder T cells.
Figure 1B:
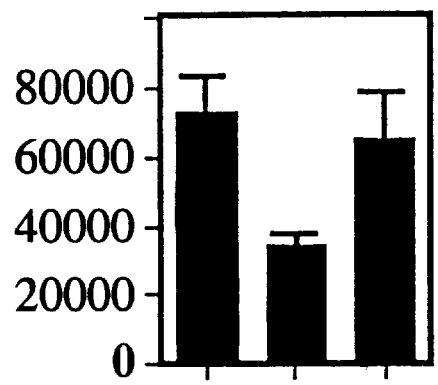

The present invention relates to a therapeutic reagent and process for treatment of subjects in need of the abrogation of immunological reactivities. The reagents and processes of the present invention are applicable to, but not limited to, the clinical settings of transplantation and autoimmunity, allergic disorders and other immunological disorders. Embodiments of the present invention include a novel T lymphocyte veto (TLV) molecule, also referred to herein as a T cell veto molecule, that regulates the activation of a responding cell by a stimulator cell, thereby suppressing an immune response.

As used herein, a stimulator cell includes any cell that, under appropriate conditions, binds to a responding cell in such a manner that the responding cell is either activated, anergized or killed. Traditional stimulator cells include "professional" antigen presenting cells (APC; e.g., dendritic cells, macrophages and B cells). According to the present invention, stimulator cells can also include a cell having a T cell veto molecule of the present invention on its surface by, for example, a tissue graft cell-specific antibody. A stimulator cell can also include a tissue graft cell, including allogeneic and xenogeneic tissue graft cells. Such graft cells can include, for example, T lymphocyte (also referred to herein as a T cell).

A responding cell includes any cell capable of being activated by a stimulator cell. Traditional responding cells include CD4–CD8+ (CD8+), CD4+CD8+, CD4–CD8–, CD4+CD8–(CD4+), αβ and γδ T cells. According to the present invention, responding cells can also include B lymphocytes (also referred to herein as B cells), as well as "naive" or "precursor" T cells. As used herein, a "naive" T cell refers to a T cell that is not activated by a T cell veto molecule of the present invention when tested using a standard effector T cell assay, such as by cytotoxic T cell (CTL) assays, T cell proliferation assays, interleukin secretion assays and assays measuring cell death (e.g., apoptosis assays). Preferably, a responding cell of the present invention includes a T cell, in particular a naive CD4+ or CD8+ T cell.

Activation of a responding cell refers to induction of signal transduction pathways in the responding cell resulting in production of cellular products (e.g., interleukin-2) by that cell. Anergy refers to the diminished reactivity by a responding cell.

Embodiments of the present invention include a novel T cell veto molecule having at least two components: (1) a responding cell activating protein (RCA protein; as defined below); and (2) a stimulator cell marker molecule (SCM molecule; as defined below) that differentiates a stimulator cell from a responding cell, in one embodiment, a host cell from a tissue graft cell. As used herein, the term "targeting polypeptide" is synonymous with the term SCM molecule. The two components of a T cell veto molecule of the present invention are associated with each other, such as by being linked by chemical or peptide binds (described in detail below).

As noted, a T cell veto molecule of the present invention comprises an RCA protein an SCM molecule. It should be noted that reference herein to an RCA protein, an SCM molecule or specific embodiments thereof, such as a CD4 protein in the case of an RCA protein, refers to the full length protein or molecule as well as a portion of a protein or molecule (e.g., non-protein with similar binding characteristics) that is at least sufficient to have the functional aspects of the referenced protein or molecule. Therefore, such a reference can refer to a full-length or partial polypeptide sequence that is capable of performing a desired function. For example, reference to a "CD4 protein" includes any portion of a CD4 molecule that is capable of binding to a CD4 co-receptor under conditions in which a complete CD4 protein binds to a co-receptor, and is capable of being linked to an SCM molecule. Similarly, a "CD2 protein" includes any portion of a CD2 molecule that is capable of binding to a CD2 co-receptor under conditions in which a complete CD2 protein binds to a co-receptor, and is capable of being linked to an SCM molecule. In addition, an SCM molecule includes any portion of a specific SCM molecule that is capable of binding to a molecule on the surface of a cell under conditions in which a complete SCM molecule would bind to a molecule on the surface of a cell, and is capable of being linked to an RCA protein of the present invention.

An RCA protein and an SCM molecule useful for the present invention is derived from an animal including, but not limited to, a human, a non-human primate, a pig, a mouse, a rat, a hamster, a rabbit, a horse and a goat, and preferably a human, a baboon and a pig.

A suitable RCA protein of the present invention comprises a protein that is capable of interfacing with a stimulator cell activating a responding cell in such manner that the action of the responding cell is altered. The resulting action of the responding cell can be inability of the responding cell to bind to a stimulator cell, apoptosis or anergy. According to the present invention, an RCA protein is preferably able to regulate the activity of a T lymphocyte, more preferably a cytotoxic and helper T lymphocyte.

One embodiment of a responding cell activation protein of the present invention comprises a CD4 protein having one variable (V) and one constant (C2) domain. A CD4 protein of the present invention preferably comprises first and second V domains and first and second C2 domains of CD4. A CD4 protein of the present invention more preferably comprises the amino acid sequence extending from about residue 1 to about residue 203 of a processed human CD4, in which the initiating Met is residue 1. For human CD4 coding sequence, see Parnes, 1989, Adv. *Immunol.* 44: 265–311; Genbank M12807; and Swissprot P01730. A CD4 protein of the present invention even more preferably comprises the amino acid sequence disclosed in SEQ ID NO:1 and a leader sequence. A preferred leader sequence to be used with a CD4 protein of the present invention is disclosed in SEQ ID NO:29.

According to the present invention, a leader sequence is an amino acid sequence that naturally occurs at the amino terminus of a protein and functions to target the protein to a membrane for secretion. A leader sequence of the present invention can also be synthesized or isolated independently of the amino acid sequence with which the leader sequence naturally occurs. It should be noted that leader sequences of the present invention can be used with the protein with which the leader sequence naturally occurs (for example, a CD4 leader sequence with a CD4 protein), or can be interchanged with another leader sequence, including any of the leader sequences presented herein or other known leader sequences as will be known to those skilled in the art. It should also be noted that leader sequences of the present invention can be inserted anywhere into the amino acid sequences of RCA proteins of the present invention, provided that the functions of the leader sequence and the RCA are preserved.

Another embodiment of a responding cell activation protein of the present invention includes a CD2 protein having one extracellular domain of CD2 protein. A CD2 protein of the present invention preferably comprises the amino acid sequence extending from about residue 1 to about residue 208 of CD2 protein, in which the initiating Met is residue 1. For human CD2 coding sequence, see Moingean et al., 1989, *Immunol. Rev.* 111: 111–144; Genbank M16445; and Swissprot P06729. A CD2 protein of the present invention more preferably comprises the amino acid sequence disclosed in SEQ ID NO:2 and a leader sequence. A preferred leader sequence to be used with a CD2 protein of the present invention is disclosed in SEQ ID NO:30.

Another embodiment of a responding cell activation protein of the present invention includes a CD28 protein having a homodimer of the pseudo-V-region of CD28 protein. A CD28 protein of the present invention preferably comprises the amino acid sequence extending from about residue 1 to about residue 161 of CD28 protein, in which the initiating Met is residue 1. For human CD28 coding sequence, see Aruffo et al., 1987, *Proc. Nat. Acad. Sci. USA* 84: 8573–8577; Genbank J02988; and Swissprot P10747. A CD28 protein of the present invention more preferably comprises the amino acid sequence disclosed in SEQ ID NO:3 and a leader sequence. A preferred leader sequence to be used with a CD28 protein of the present invention is disclosed in SEQ ID NO:31.

Another embodiment of a responding cell activation protein of the present invention includes a cytotoxic T cell antigen 4 (CTLA4) protein having a homodimer of the pseudo V region of CTLA4 protein. A CTLA4 protein of the present invention preferably comprises the amino acid sequence extending from about residue 1 to about residue 161 of CTLA4 protein, in which the initiating Met is residue 1. For human CTLA4 coding sequence, see Danavach et al., 1988, *Eur. J. Immunol.* 18: 1901–1905; Genbank X15070; and Swissprot P16410. A CTLA4 protein of the present invention more preferably comprises the amino acid sequence disclosed in SEQ ID NO:4 and a leader sequence. A preferred leader sequence to be used with a CTLA4 protein of the present invention is disclosed in SEQ ID NO:32.

Another embodiment of a responding cell activation protein of the present invention includes a fas-ligand protein having the extracellular domain of fas-ligand protein. A fas-ligand protein of the present invention preferably comprises the amino acid sequence extending from about residue 137 to about residue 283 of fas-ligand protein, in which the initiating Met is residue 1. For human fas-ligand coding sequence, see Takahashi et al., 1994, Intern. *Immunol.* 6: 1567–1574. A fas-ligand protein of the present invention more preferably comprises the amino acid sequence disclosed in SEQ ID NO:5 and a leader sequence. An acceptable leader sequence to be used with a Fas-ligand protein of the present invention is disclosed, for example, in SEQ ID NO:29.

Another embodiment of a responding cell activation protein of the present invention includes a CD5 protein having the domains 1 through 3 of CD5 protein. A CD5 protein of the present invention preferably comprises the amino acid sequence extending from about residue 1 to about residue 372 of CD5 protein, in which the initiating Met is residue 1. For human CD5 coding sequence, see Jones et al., 1986, *Nature* 323: 346–349. A CD5 protein of the present invention more preferably comprises the amino acid sequence disclosed in SEQ ID NO:6 and a leader sequence. A preferred leader sequence to be used with a CD5 protein of the present invention is disclosed in SEQ ID NO:33.

Another embodiment of a responding cell activation protein of the present invention includes a CD7 protein having the pseudo V region of CD7 protein. A CD7 protein of the present invention preferably comprises the amino acid sequence extending from about residue 1 to about residue 180 of CD7 protein, in which the initiating Met is residue 1. For human CD7 coding sequence, see Aruffo et al., 1987, *EMBO J.* 6: 3313–3316; Genbank X06180; and Swissprot P09564. A CD7 protein of the present invention more preferably comprises the amino acid sequence disclosed in SEQ ID NO:7 and a leader sequence. A preferred leader sequence to be used with a CD7 protein of the present invention is disclosed in SEQ ID NO:34.

Another embodiment of a responding cell activation protein of the present invention includes a CD9 protein having the extracellular domain of CD9 protein. A CD9 protein of the present invention preferably comprises the amino acid sequence extending from about residue 113 to about residue 192 of CD9 protein, in which the initiating Met is residue 1. For human CD9 coding sequence, see Boucheix et al., 1990, *J. Biol. Chem.* 266: 117–122; Genbank M38690; and Swissprot P21926. A CD9 protein of the present invention more preferably comprises the amino acid sequence disclosed in SEQ ID NO:8 and a leader sequence. An acceptable leader sequence to be used with a CD9 protein of the present invention is disclosed, for example, in SEQ ID NO:29.

Another embodiment of a responding cell activation protein of the present invention includes a CD11 protein having the CD13 alpha extracellular domain complexed with the CD18 extracellular domain of the CD11 protein. A CD11 alpha protein of the present invention preferably comprises the amino acid sequence extending from about residue 1 to about residue 1089 of CD11 alpha protein, in which the initiating Met is residue 1. For human CD11 alpha coding sequence, see Larson et al., 1990, *Immunol. Rev.* 114: 181–217; Genbank Y00796; and Swissprot P20701. A CD11 protein of the present invention more preferably comprises the amino acid sequence disclosed in SEQ ID NO:9 and a leader sequence. A preferred leader sequence to be used with a CD11 protein of the present invention is disclosed in SEQ ID NO:35.

Another embodiment of a responding cell activation protein of the present invention includes a CD18 protein having the extracellular domain of CD18 protein. A CD18 protein of the present invention preferably comprises the amino acid sequence extending from about residue 1 to about residue 750 of CD18 protein, in which the initiating Met is residue 1. For human CD18 coding sequence, see Larson et al., 1990, *Immunol. Rev.* 114: 181–217; Genbank Y00057; and Swissprot P05107. A CD18 protein of the present invention more preferably comprises the amino acid sequence disclosed in SEQ ID NO:10 and a leader sequence. A preferred leader sequence to be used with a CD18 protein of the present invention is disclosed in SEQ ID NO:36.

Another embodiment of a responding cell activation protein of the present invention includes a CD27 protein having the extracellular domain of CD27 protein. A CD27 protein of the present invention preferably comprises the amino acid sequence extending from about residue 1 to about residue 191 of CD27 protein, in which the initiating Met is residue 1. For human CD27 coding sequence, see Camerinin et al., 1991, *J. Immunol.* 147: 3165–3169; Genbank M62928. A CD27 protein of the present invention more preferably comprises the amino acid sequence disclosed in SEQ ID NO:11 and a leader sequence. A preferred leader sequence to be used with a CD27 protein of the present invention is disclosed in SEQ ID NO:37.

Another embodiment of a responding cell activation protein of the present invention includes a CD43 protein having the extracellular domain of CD43 protein. A CD43 protein of the present invention preferably comprises the amino acid sequence extending from about residue 1 to about residue 384 of CD43 protein, in which the initiating Met is residue 1. For human CD43 coding sequence, see Pallant et al., 1989, *Proc. Nat. Acad. Sci. USA* 86: 1328–1332; Genbank J04168; and Swissprot 16150. A CD43 protein of the present invention more preferably comprises the amino acid sequence disclosed in SEQ ID NO:12 and a leader sequence. A preferred leader sequence to be used with a CD43 protein of the present invention is disclosed in SEQ ID NO:38.

Another embodiment of a responding cell activation protein of the present invention includes a CD45 protein comprising an extracellular domain of an isoform of a CD45 protein. A CD45protein of the present invention preferably comprises the amino acid sequence extending from about residue 1 to about residue 556 of CD45 protein, in which the initiating Met is residue 1. For human CD45 coding sequence, see Streuli et al., 1987, *J.Exp. Med.* 166: 1548–1566; Genbank Y00638; and Swissprot P08575. According to the present invention, an isoform of a CD45 protein is any CD45 protein that is formed by the alternative splicing of exons A, B, and C of CD45; such isoforms are well known to those skilled in the art. CD45 isoforms of the present invention include an isoform in which none of the exons are spliced out, an isoform in which all of the exons are spliced out, an isoform in which any one of exons A, B, or C is spliced out, and an isoform in which any combination of exons A, B, and C are spliced out. A CD45 protein of the present invention more preferably comprises any isoform of the amino acid sequence disclosed in SEQ ID NO:13 and a leader sequence. A preferred leader sequence to be used with a CD45 protein of the present invention is disclosed in SEQ ID NO:39.

Another embodiment of a responding cell activation protein of the present invention includes a CD48 protein having a pseudovariable and a pseudoconstant extraellular domains of CD48 protein. A CD48 protein of the present invention preferably comprises the amino acid sequence extending from about residue 1 to about residue 220 of CD48 protein, in which the initiating Met is residue 1. For human CD48 coding sequence, see Killeen et al., 1988, *EMBO J.* 7: 3087–3091; Genbank X06341, M37766, M59904; and Swissprot P09326. A CD48 protein of the present invention more preferably comprises the amino acid sequence disclosed in SEQ ID NO:14 and a leader sequence. A preferred leader sequence to be used with a CD48 protein of the present invention is disclosed in SEQ ID NO:40.

Another embodiment of a responding cell activation protein of the present invention includes a B7.1 protein having a pseudovariable and a pseudoconstant extracellular domain of B7.1 protein. A B7.1 protein of the present invention preferably comprises the amino acid sequence extending from about residue 1 to about residue 242 of B7.1 protein, in which the initiating Met is residue 1. For human B7.1 coding sequence, see Freeman et al., 1989, *J. Immunol.* 143: 2714–2722; Genbank M27533. A B7.1 protein of the present invention more preferably comprises the amino acid sequence disclosed in SEQ ID NO:15 and a leader sequence. A preferred leader sequence to be used with a B7.1 protein of the present invention is disclosed in SEQ ID NO:41.

Another embodiment of a responding cell activation protein of the present invention includes a B7.2 protein having an extracellular domain of B7.2 protein. A B7.2 protein of the present invention preferably comprises the amino acid sequence extending from about residue 1 to about residue 74 of B7.2 protein, in which the initiating Met is residue 1. For human B7.2 coding sequence, see Kubota et al., 1990, *J. Immunol.* 145, 3924–3931; Genbank M55561. A B7.2 protein of the present invention more preferably comprises the amino acid sequence disclosed in SEQ ID NO:16 and a leader sequence. An acceptable leader sequence to be used with a B7.2 protein of the present invention is disclosed, for example, in SEQ ID NO:29.

It is within the scope of the present invention that an RCA protein can be a portion of CD8 comprising a peptide that is capable of binding to a MHC Class I molecule in such a manner that cytotoxic T cell activity is regulated.

According to the present invention, at least a portion of an RCA protein of the present invention can be linked to at least a portion of an immunoglobulin (Ig) molecule to form an RCA:Ig chimeric molecule. An RCA protein is preferably linked to an Ig molecule by a peptide bond, which refers to the covalent chemical interaction between two amino acids. A preferred portion of an Ig molecule to link to an RCA protein includes the constant region of an immunoglobulin molecule. Suitable $C_L$ and $C_H$ regions for use with an RCA:Ig chimeric molecule of the present invention include κ, λ, μ, γ1, γ2, γ2a, γ2b, γ3, γ4, α, α1, α2, σ and ε constant regions, with human κ, λ, μ, γ1, γ2, γ3, γ4, α1, α2, σ and ε constant regions being more preferred and human IgG2a being even more preferred. Any constant region of any antibody is suitable for use with the present invention. A preferred portion of a constant region to use includes at least one amino acid that enables an RCA:Ig molecule to be di-sulfide bonded to an SCM molecule of the present invention.

In a preferred embodiment, an RCA:Ig chimeric molecule of the present invention comprises a CD4:Ig chimeric molecule having the amino acid sequence disclosed in SEQ ID NO:17 and a leader sequence. A preferred leader sequence to be used with a CD4:Ig protein of the present invention is disclosed in SEQ ID NO:29.

In another preferred embodiment, an RCA:Ig chimeric molecule of the present invention comprises a CD2:Ig chimeric molecule having the amino acid sequence disclosed in SEQ ID NO:18 and a leader sequence. A preferred leader sequence to be used with a CD2:Ig protein of the present invention is disclosed in SEQ ID NO:30.

In another preferred embodiment, an RCA:Ig molecule of the present invention comprises a CD28:Ig chimeric molecule having the amino acid sequence disclosed in SEQ ID NO:19 and a leader sequence. A preferred leader sequence to be used with a CD28:Ig protein of the present invention is disclosed in SEQ ID NO:31.

In another preferred embodiment, an RCA:Ig chimeric molecule of the present invention comprises a CTLA4:Ig molecule having the amino acid sequence disclosed in SEQ ID NO:20 and a leader sequence. A preferred leader sequence to be used with a CTLA4:Ig protein of the present invention is disclosed in SEQ ID NO:32.

In another preferred embodiment, an RCA:Ig chimeric molecule of the present invention comprises a fas-ligand:Ig chimeric molecule having the amino aid sequence disclosed in SEQ ID NO:21 and a leader sequence. An acceptable leader sequence to be used with a Fas-ligand:Ig protein of the present invention is disclosed, for example, in SEQ ID NO:29.

One embodiment of a stimulator cell marker (SCM) molecule of the present invention includes a molecule capable of targeting an RCA protein of the present invention to a desired cell. In particular, an SCM molecule of the present invention includes, but is not limited to an immunoglobulin molecule (an antibody), a growth factor or a tissue-specific antigen. A suitable antibody for use as an SCM molecule of the present invention binds to a protein on the surface of a stimulator cell of the present invention. A preferred antibody of the present invention binds to a protein on the surface of a tissue graft cell or a cell involved in an autoimmune response. A more preferred antibody of the present invention binds to a major histocompatibility molecule (MHC), including Class I and Class II, or an organ-specific molecule, such as molecules expressed on the surface of kidney cells (e.g., sodium-potassium-chloride cotransporters; see Herbert et al., 1994, *Clin. Invest.* 72: 692–694), liver cells (e.g., asialoglycoprotein receptor; see Merwin et al., 1994, *Bioconjugate Chem.* 5: 612–620; bile acid receptors; see Krmaer et al., 1992; *J. Bio. Chem.* 267: 18598–18604; LMA surface target molecules; see Stemerowicz et al., 1990, *J.Clin. Lab. Immunol.* 32: 13–19); heart cells (e.g., heart specific auto-antibodies; see Neumann, et al., 1992, *J. Immunol.* 148: 3806–3813; Traystman et al., 1991, *Clin. Exp. Immunol.* 86: 291–298); pancreas cells or bone marrow cells (e.g., c-kit receptor; see Okayama et al., 1994, *J. Immunol. Meth.* 169: 153–161; Bridell et al., 1992, *Blood* 79: 3159–3167.

In a preferred embodiment, an antibody useful as an SCM molecule of the present invention includes the immunoglobulin molecules WFL4F12.3, WFL3C6.1, BB7.2, PA2.1, 2.28M1, MA2.1, GAP A3, A11.1M, 4D12, BB7.1, B27M1, ME1, BB7.6, MB40.2, MB40.2, B27M2, SFR8-B6, Genox 3.53, G2a.5 and SFR3-DR5 (each described in ATCC Catalogue of Cell Lines and Hybridomas, 7th Edition, 1992 American Type Culture Collection).

It is within the scope of the present invention that an antibody can include a full-length antibody, an Fab fragment, an F(ab')$_2$ fragment or an F$_V$ fragment of an antibody. An Fab fragment comprises one arm of an immunoglobulin molecule containing a light chain (V$_L$ region+C$_L$ region) paired with the heavy chain variable region (V$_H$ region) and a portion of a heavy chain constant region (C$_H$ region) CH1 domain. An F(ab')$_2$ fragment corresponds to two di-sulfide bonded arms of an immunoglobulin molecule, each arm containing a L chain (V$_L$ region+C$_L$ region) paired with a V$_H$ region and a CH1 domain. An F$_V$ fragment refers to a portion of an immunoglobulin molecule V$_L$ region paired with a V$_H$ region. Thus, an antibody of the present invention can include the variable (V), diversity (D) and junction (J) regions, the V, D, J and CH1 regions or the full-length protein of any preferred antibody described herein.

A suitable growth factor for use as an SCM molecule of the present invention binds to a receptor on the surface of a stimulator cell of the present invention. A preferred growth factor of the present invention binds to a receptor on the surface of a tissue graft cell or a cell involved in an autoimmune response. A more preferred growth factor of the present invention includes, but is not limited to thyroid stimulating hormone (TSH), vasopressin or corticotropin.

A suitable growth factor for use as an SCM molecule of the present invention binds to a tissue-specific marker on the surface of a stimulator cell of the present invention. A preferred SCM molecule of the present invention binds to a tissue specific marker on the surface of a tissue graft cell or a cell involved in an autoimmune response. A more preferred SCM molecule of the present invention includes, but is not limited to asialoglycoprotein receptor, (TSH) receptor, vasopressin receptor or corticotropin receptor.

According to the present invention, an RCA protein or an SCM molecule can comprise a derivative of an RCA protein or an SCM molecule. In accordance with the present invention, a "derivative" refers to any compound that is able to mimic the ability of a component of an RCA protein or an SCM molecule of the present invention. A derivative of an RCA protein or an SCM molecule can be an amino acid sequence that has been modified to decrease its susceptibility to degradation but that still retains binding activity. Other examples of derivatives include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof having desired T cell regulatory activity. A derivative can be obtained by, for example, screening libraries of natural and synthetic compounds for compounds capable of binding to a CD4 or CD2 co-receptor or an MHC antigen, as disclosed herein. A derivative of a CD4, CD2 or immunoglobulin molecule can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential derivatives by, for example, computer modelling. The predicted derivative structures can then be produced by, for example, chemical synthesis, recombinant DNA technology, or by isolating a mimetope from a natural source (e.g., plants, animals, bacteria and fungi).

In particular, a derivative of an RCA protein or an SCM molecule can include amino acid substitution or insertion mutants into which an amino acid has been substituted or inserted, the amino acid being capable of forming a di-sulfide bond with another amino acid (e.g., a cysteine or a proline).

An RCA protein or an SCM molecule of the present invention can be soluble or membrane-bound. Amino acid sequences can be genetically engineered to create soluble forms by introducing a translational stop codon into the coding sequences of an RCA protein or an SCM molecule, upstream of the cytoplasmic domains and/or the hydrophobic transmembrane domains, using technologies known to those of skill in the art (e.g., site-directed mutagenesis or PCR modification). An example of a soluble CD4 molecule includes SEQ ID NO:17. An example of a soluble CD2 molecule includes SEQ ID NO:18. The resulting truncated CD4- or CD2-encoding nucleic acid molecules can be operatively linked to an expression vector containing one or more transcription or translation control regions to form a recombinant molecule, and the recombinant molecules can be expressed in a host cell.

Amino acid sequences can be genetically engineered to create membrane-bound forms by linking, or retaining the linkage of, the amino acid sequences of an RCA protein or an SCM molecule to amino acid sequences for transmembrane domains and/or amino acid sequences for cytoplasmic domains. Preferably, a membrane-form of an RCA protein or an SCM molecule of the present invention is designed such that the molecule can be inserted into the plasma membrane of a cell and remain associated with the membrane over time. An embodiment of a plasma membrane-bound form of an RCA protein or an SCM molecule preferably comprises a full-length transmembrane domain and cytoplasmic domain of an RCA protein or an SCM molecule. Such membrane-bound forms can be produced by operatively linking nucleic acid molecules encoding full-length RCA protein or SCM molecule to an expression vector containing one or more transcription or translation control regions to form a recombinant molecule, and expressing the recombinant molecules in a host cell. Alternatively, an RCA protein or an SCM molecule can be designed such that the molecule can be anchored in a lipid bilayer when incorporated into lipid-containing substrates by being added exogenously. As used herein, the term "anchoring" refers to the insertion of a molecule in a lipid-containing substrate such that any extracellular domains are on the outside of the substrate.

In one embodiment, an RCA protein or an SCM molecule of the present invention is produced by culturing a cell transformed with a recombinant molecule comprising a nucleic acid molecule operatively linked to an expression vector, in which the nucleic acid molecule comprises a nucleic acid sequence encoding an RCA protein or an SCM molecule.

A recombinant molecule of the present invention comprises a nucleic acid molecule, encoding an RCA protein or an SCM molecule of the present invention, operatively linked to a vector capable of being expressed in a host cell. As used herein, "operatively linked" refers to insertion of a nucleic acid sequence into an expression vector in such a manner that the sequence is capable of being expressed when transformed into a host cell. As used herein, an "expression vector" is an RNA or DNA vector capable of transforming a host cell and effecting expression of an appropriate nucleic acid sequence, preferably replicating within the host cell. An expression vector can be either prokaryotic or eukaryotic, and typically is a virus or a plasmid.

Construction of desired expression vectors can be performed by methods known to those skilled in the art and expression can be in eukaryotic or prokaryotic systems. Procaryotic systems typically used are bacterial strains including, but not limited to various strains of *E. coli*, various strains of *bacilli* or various species of Pseudomonas. In prokaryotic systems, plasmids are used that contain replication sites and control sequences derived from a species suitable for use with a host cell. Control sequences can include, but are not limited to promoters, operators, enhancers, ribosome binding sites, and Shine-Dalgarno sequences. Expression systems useful in eukaryotic host cells comprise promoters derived from appropriate eukaryotic genes. Useful mammalian promoters include early and late promoters from SV40 or other viral promoters such as those derived from baculovirus, polyoma virus, adenovirus, bovine papilloma virus or avian sarcoma virus. Expression vectors of the present invention include any vectors that function (i.e., direct gene expression) in recombinant cells of the present invention including bacterial, yeast, other fungal, insect and mammalian cells. Preferred expression vectors of the present invention include vectors containing immunoglobulin H chain promoters and/or L chain promoters. In particular, an expression vector of the present invention includes a polyhedrin promotor for CD4 or CD2 for use in a baculovirus expression system or a CMV immediate early promotor or a RSV-LTR promotor for use in a eukaryotic cell system. Useful mammalian enhancers include immunoglobulin H chain enhancers and/or L chain enhancers. Particularly preferred expression vectors for use with the present invention include baculovirus transfer vectors pVL1393, pAcUw51or pAcAB3. In a preferred embodiment, an expression vector of the present invention comprises pVLCD2-IgG2a or pVLCD4-IgG2a.

An expression system can be constructed from any of the foregoing control elements operatively linked to the nucleic acid sequences of the present invention using methods known to those of skill in the art (see, for example, Sambrook et al., ibid.).

Host cells of the present invention can be cells naturally capable of producing an RCA protein or an SCM molecule, or cells that are capable of producing an RCA protein or an SCM molecule when transfected with a nucleic acid molecule encoding such molecules. Host cells of the present invention include, but are not limited to bacterial, fungal, insect and mammalian cells. Suitable host cells include mammalian cell, preferably a fibroblast, a pluripotent progenitor cell, an epithelial cell, a neural cell, a T cell line and a B cell line.

In one embodiment, a host cell is transformed with: (1) a first recombinant molecule comprising a nucleic acid molecule operatively linked to an expression vector, the nucleic acid molecule having a sequence encoding a first protein including an RCA protein, particularly CD4, CD2, CD28, CTL4A, fas-ligand, CD5, CD7, CD9, CD11, CD18, CD27 CD43, CD45, CD48, B7.1 and B7.2, and even more particularly CD4, CD2, CD28, CTL4A, fas-ligand; and (2) a second recombinant molecule comprising a nucleic acid molecule operatively linked to an expression vector, the nucleic acid molecule having a sequence encoding a second protein comprising a stimulatory cell marker molecule that differentiates a host cell from a tissue graft cell to form a recombinant cell.

Transformed recombinant cells of the present invention are cultured under conditions effective to produce such an RCA protein and SCM molecule. The protein and molecule can then be recovered from the culture medium and/or the cells. Effective conditions to produce an RCA or SCM molecule include, but are not limited to appropriate culture media, cell density, temperature, pH and oxygen conditions. One of skill in the art can choose appropriate culture conditions based on the type of cell being cultured and the amount of protein one desires to produce.

Depending on the expression vector used for production, resultant molecules can either remain within the recombinant cell, be retained on the outer surface of the recombinant cell, or be secreted into the culture medium. As used herein, the term "recovering" refers to collecting the culture medium containing the molecule and/or recombinant cells. Recovery need not imply additional steps of separation or purification.

After recovery, an RCA protein or SCM molecule can be purified using a variety of standard protein purification techniques such as, but not limited to, size separation chromatography, reverse phase chromatography, chromatofocussing, hydroxyapatite adsorption and electrophoresis systems, affinity chromatography, ion exchange chromatography, ammonium sulfate precipitation, filtration, centrifugation, hydrophobic interaction chromatography, gel filtration chromatography, high pressure liquid chromatography and differential solubilization. Isolated proteins are preferably retrieved in substantially pure form. As used herein, "substantially pure" refers to a purity that allows for the effective use of the molecule as a heretofore described T cell veto molecule.

Soluble RCA proteins or SCM molecules of the present invention can be purified using, for example, immunoaffinity chromatography using an antibody capable of binding to CD4, CD2, CD28, CTL4A, fas-ligand or the C region of an immunoglobulin molecule or an antigen capable of binding to the V region of immunoglobulin molecule. RCA proteins or SCM molecules anchored in a lipid-containing substrate can be recovered by, for example, density gradient centrifugation techniques.

One aspect of the present invention is a method for producing a T cell veto molecule, comprising: (a) providing a first protein comprising an RCA protein, in particular CD4, CD2, CD28, CTL4A, fas-ligand protein, CD5 protein, CD7 protein, CD9 protein, CD11 protein, CD18 protein, CD27 protein, CD43 protein, CD45 protein, CD48 protein, B7.1 protein and B7.2 protein; (b) providing a second protein comprising an SCM molecule; and (c) linking the first protein to the second protein to form a chimeric molecule. As used herein, the term "linked" can refer to covalently attaching an RCA protein to an SCM molecule. A suitable reagent for the linking step includes any reagent capable of creating di-sulfide bonds between an RCA protein and an SCM molecule. Preferably, an RCA protein can be covalently associated to an SCM molecule by several methods including, for example, treatment with chemicals capable of linking di-sulfide bonds, glutaraldehyde linkage, photoaffinity labelling, treatment with carbodiimides and treatment with other cross-linking chemicals standard in the art. Preferably, an RCA protein can be covalently associated to an SCM molecule by treatment with chemicals capable of linking di-sulfide bonds, in particular using N-succinimidyl-3-1-(1-pyridyldthio)-propionate.

Following chemical cross-linking of an RCA protein to an SCM molecule, the resulting chimeric T cell veto molecules are recovered from those proteins that have not been linked using methods standard in the art. Preferably, T cell veto molecules are recovered by size separation chromatography.

A T cell veto molecule of the present invention preferably comprises a CD4:Ig protein having the amino acid sequence represented by SEQ ID NO:17, di-sulfide bonded to an antibody that binds specifically to an MHC molecule, in particular 14-4-4 to form the CD4:14 T cell veto molecule (see Examples section). A T cell veto molecule of the present invention also preferably comprises a CD2:Ig having the amino acid sequence represented by SEQ ID NO:18, di-sulfide bonded to an antibody that binds specifically to an MHC molecule, in particular 14-4-4 to form the CD2:14 T cell veto molecule.

According to the present invention, different embodiments of a T cell veto molecule of the present invention can be combined to form a composition of the present invention. A preferred composition comprises a CD4 protein linked to a target molecule that differentiates a host cell from a tissue graft cell, a chimeric molecule having a CD2 protein linked to target molecule that differentiates a host cell from a tissue graft cell, a chimeric molecule having a CD28 protein linked to target molecule that differentiates a host cell from a tissue graft cell, a chimeric molecule having a CTL4A protein linked to target molecule that differentiates a host cell from a tissue graft cell, a chimeric molecule having a fas-ligand protein linked to target molecule that differentiates a host cell from a tissue graft cell and mixtures thereof. A more preferred composition comprises CD4:14 T cell veto molecule, CD2:14 T cell veto molecule and mixtures thereof.

Another aspect of the present invention comprises formulating a T cell veto molecule of the present invention with a pharmacologically acceptable carrier to form a therapeutic composition of the present invention. As used herein, a "carrier" refers to any substance suitable as a vehicle for delivering a T cell veto molecule to a suitable in vitro or in vivo site of action. As such, carriers can act as an excipient for formulation of a therapeutic or experimental reagent containing a T cell veto molecule. Preferred carriers are capable of maintaining a T cell veto molecule in a form that is capable of binding to a stimulating cell and regulating the activity of a responding cell. Examples of such carriers include, but are not limited to water, phosphate buffered saline, saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer and bicarbonate buffer. Auxiliary substances can also include preservatives, such as thimerosal, m or o-cresol, formalin and benzyl alcohol. Preferred auxiliary substances for aerosol delivery include surfactant substances nontoxic to a recipient, for example, esters or partial esters of fatty acids containing from about 6 to about 22 carbon atoms. Examples of esters include, caproic, octanoic, lauric, palmitic, stearic, linoleic, linolenic, olesteric and oleic acids. Therapeutic compositions of the present invention can be sterilized by conventional methods and/or lyophilized. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

A therapeutic composition can further comprise a T cell veto molecule combined with a compound capable of suppressing an immune response. Such regulatory compounds include, but are not limited to, immunosuppressive drugs or antibodies that specifically bind to interleukins.

Useful carriers for membrane-bound T cell veto molecules include any artificial or natural lipid-containing substrate, preferably cells, cellular membranes, liposomes and micelles. Cellular carriers of the present invention include cells capable of producing a T cell veto molecule. Preferred cells are disclosed in detail herein.

Embodiments of the present invention comprise the use of a T cell veto molecule, as disclosed in the present invention, to suppress the activity of immune cells in vivo or in vitro. In particular, a T cell veto molecule of the present invention is useful for administration to subjects to immunosuppress subjects against, for example, autoantigens, allergens, engraftments and agents perfused into subjects (i.e., blood factors and platelets). This process is particularly applicable for purposes of specific immunosuppression, and derives from the novel structure of a T cell veto molecule of the present invention. Immune cells refers to cells typically involved in an immune response (e.g., T cells, APCs etc.). Immunosuppression refers to inhibiting an immune response by, for example, killing or anergizing (i.e., diminishing reactivity by a T cell to an antigenic peptide) particular cells involved in the immune response.

One aspect of the present invention is a method to suppress an immune response comprising: (a) providing a chimeric molecule having a protein, selected from the group consisting of CD4, CD2, CD28, CTL4A, fas-ligand, CD5 protein, CD7 protein, CD9 protein, CD11 protein, CD18 protein, CD27 protein, CD43 protein, CD45 protein, CD48 protein, B7.1 protein and B7.2 protein linked to a responding cell marker molecule; and (b) exposing the chimeric molecule to an antigen presenting cell that can respond to the chimeric molecule, for a time and under conditions sufficient to reduce a cellular immune response of a T lymphocyte to an antigen. The present method is particularly useful for reducing the response of a T cell to an antigen comprising an alloantigen or a processed antigen.

Preferably, the chimeric molecule is contacted with the antigen presenting cell in vivo. Acceptable protocols to administer therapeutic compositions in vivo in an effective manner include individual dose size, number of doses, frequency of dose administration and mode of administration. Determination of such protocols can be accomplished by those skilled in the art depending upon a variety of variables, including the animal to be treated, the type of treatment being administered (e.g., graft rejection prevention or treatment of an autoimmune disease) and the stage of disease.

Effective doses to immunosuppress an animal include doses administered over time that are capable of alleviating an immune response by the animal. For example, a single suppressing dose can comprise an amount of a therapeutic composition of the present invention that sufficiently ablates an immune response against an alloantigen, compared with an immune response in the absence of the therapeutic composition. Alternatively, a single suppressing dose can comprise an amount of a therapeutic composition of the present invention that partially reduces an immune response against an alloantigen, compared with an immune response in the absence of the therapeutic composition. In this case, repeated administrations of the single dose could be given to an animal until the immune response is sufficiently ablated. A suitable single dose of a therapeutic composition of the present invention is a dose that is capable of substantially inhibiting a T cell response to an antigen when administered one or more times over a suitable time period. A single dose of a therapeutic composition preferably ranges from about 1 micrograms ($\mu$g) to about 100 milligrams (mg), more preferably ranges from about 10 $\mu$g to about 10 mg and even more preferably ranges being from about 100 $\mu$g to about 1 mg of a therapeutic composition per subject, of a toleragenic therapeutic reagent per subject. Effective doses to suppress an animal include doses administered over time that are capable of decreasing T cell activation to an antigen by an animal. For example, a first suppressing dose can comprise an amount of a therapeutic composition of the present invention that prevents an immune response when administered to an animal. A second suppressing dose can comprise a lesser amount of the same therapeutic composition than the first dose to continue prevention of an immune response. For example, if a first dose can comprise about $10^6$ arbitrary units of a TLV molecule, then a second dose can comprise about $10^3$ arbitrary units of a TLV molecule.

Effective suppressing doses can comprise decreasing concentrations of a therapeutic composition of the present invention necessary to maintain an animal in a suppressed state, such that the animal does not have an immune response to subsequent exposure to an antigen.

The manner of administration of a therapeutic composition of the present invention can depend upon the particular purpose for the delivery (e.g., treatment of disease or prevention of graft rejection), the overall health and condition of the recipient and the judgement of the physician or technician administering the therapeutic composition. A therapeutic composition of the present invention can be administered to an animal using a variety of methods. Such delivery methods can include parenteral, topical, oral or local administration, such as intradermally or by aerosol. A therapeutic composition can be administered in a variety of unit dosage forms depending upon the method of administration. For example, unit dosage forms suitable for oral administration to the intestinal region of an animal include powder, tablets, pills and capsules. Preferred delivery methods for a therapeutic composition of the present invention include intravenous administration and local administration by, for example, injection or topical administration. For particular modes of delivery, a therapeutic composition of the present invention can be formulated in an excipient of the present invention. A therapeutic reagent of the present invention can be administered to any animal, preferably to mammals, and more preferably to humans.

As an example of a T cell veto molecule-mediated immunosuppressive therapeutic process, the sequence of steps that can be executed for inducing suppression in a prospective transplant recipient for the allogeneic MHC molecule of the transplant donor, in order to prevent immunological rejection of the graft following transplantation, are as follows:

(a) gene constructs are assembled for producing human CD4, human CD2 and specific antibodies that bind to MHC Class II molecules. In each case, the coding sequence for the extracellular domain of CD4 or CD2 is subcloned into pVL1393 vector.

(b) The subcloned coding sequences are transfected into insect cells in order to produce recombinant CD4, CD2 and immunoglobulin protein. The transfected cells are maintained in serum-free, protein-free medium.

(c) Dimers of soluble human CD4 or human CD2 are harvested from the cell cultures by the following method. Tissue culture supernatant, adjusted to pH 8.5, is filtered through a Mono-Q-Sepharose column (Pharmacia, Uppsala, Sweden). The flow-though is loaded onto a Wheatgerm-Lectin-Sepharose column (Pharmacia), and CD4 or CD2 are eluted with 5% N-acetyl-glucosamine. The eluate is dialyzed against 20 mM $NaC_2H_3O_2$ (pH 5.4, Sigma), concentrated and loaded onto Mono-S-Sepharose (Pharmacia) pre-equilibrated with 20 mM HEPES (pH 8.0, Sigma). Soluble CD4 or CD2 is eluted as the first peak of a NaCl-gradient (20 mM to 500 mM, Sigma) in 20 mM HEPES (pH 8.0) and dialyzed against PBS. The purity of the CD4 or CD2 dimers is analyzed by resolution using SDS-PAGE gel electrophoresis. Immunoglobulin molecules are purified from tissue-culture supernatant on a Protein A-Sepharose column (Pharmacia) using a standard protocol.

(d) Soluble CD4 or CD2, and immunoglobulin are cross-linked using the heterobifunctional cross-linker, N-succinimidyl-3-(1-pyridyldithio)-propionate (SPDP, Pharmacia) according to standard methods, at pH 7.4. Cross-linked proteins are purified from unreacted proteins and SPDP by passage of the preparation over on a Sephadex G25 column (Pharmacia).

(e) A subject who is to undergo a transplant is assessed for alloreactivity to donor allo-MHC by isolating peripheral blood mononuclear cells (PBMC) from the prospective transplant recipient's blood, and setting up a mixed lymphocyte reaction (MLR) with the recipient's PBMC as responders and irradiated (1500 rads) donor PBMC as stimulators. If a significant proliferative response is noted, a therapeutic composition comprising a TLV molecule or composition thereof, corresponding to the donor allo-MHC, are infused intravenously into the graft recipient about 4 to about 1 weeks prior to the planned transplantation procedure.

(f) At about 2 to about 1 weeks prior to the transplantation date, the MLR is repeated, and if a residual proliferative response between recipient responders and donor stimulators persists, the therapeutic composition is reinfused into the graft recipient.

(g) The MLR is repeated post-transplantation to assess the need for booster doses to the graft recipient of a therapeutic composition which can be administered systemically or topically, as required.

Another example of a TLV molecule-mediated immunosuppressive therapeutic process, the sequence of steps (a) through (d) from the foregoing example are repeated and the cells of a graft are coated with a therapeutic composition of the present invention, and then the graft is transplanted into a recipient. The process is applicable to a variety of graft types, including vascularized solid tissue (e.g., kidney, heart, liver, lung and skin) and dispersed cellular populations (e.g., bone marrow cells). Treatment of a solid graft can comprise the steps of: (1) perfusing the donor organ at the time of surgery and prior to its resection, with about 100 µg/ml of a therapeutic composition comprising TLV molecules contained in normal saline via a bolus injection into a vessel entering the organ; and (2) catherizing the vessel, resecting the organ and storing the organ in a solution supplemented with a therapeutic composition of the present invention until transplantation. Treatment of a dispersed cell population can comprise the steps of: (1) aspirating a cell population from a donor and separating the cells from undesired blood elements using methods standard in the art; and (2) resuspending the isolated donor cells in about 10 µg/ml of a therapeutic composition comprising TLV molecules contained in normal saline for about 2 hours at 5° C. until transplantation.

It is within the scope of the invention that the pre-treatment of a recipient and the treatment of a graft tissue can be performed separately or in combination, depending on the parameters of the transplantation (e.g., donor-recipient allotype match, type of tissue etc.). It is also within the scope of the present invention that modifications can be made to the therapeutic processes disclosed herein. For example, subjects afflicted with autoimmune disease can treated by systemically administering a therapeutic composition of the present invention using similar steps as those outlined for the pre-treatment of graft recipients. Alternatively, a therapeutic composition can be administered to subjects afflicted with localized autoimmune diseases, such as rheumatoid arthritis, by directly injecting the composition into a diseased area such as a joint. Other examples of autoimmune diseases that can be treated using a therapeutic composition of the present invention include systemic lupus erythematosus, myasthenia gravis, rheumatoid arthritis, insulin-dependent diabetes mellitus, multiple sclerosis, celiac disease, autoimmune thyroiditis, Addison's disease, Graves' disease and rheumatic carditis.

One embodiment of a therapeutic method of the present invention includes administering a high dose of corticosteroids, for example dexamethason in two injections (about 1 mg per day for two days, followed by the step of administering a T cell veto molecule of the present invention for the next four weeks, at a concentration of about 1 mg per injection (intravenous) twice a week.

The following experimental results are provided for purposes of illustration and are not intended to limit the scope of the invention.

EXAMPLES

Example 1

This example describes the production of chimeric cDNA clones encoding CD2:Ig or CD4:Ig molecules.

A. Production of Human Blood or 15.5.5. cDNA

Two separate samples of cDNA were prepared using mRNA isolated from human blood or 15.5.5 cells (described in Ozato et al., 1980, *J. Immunol.* 124: 533) by the following method. About 2 mL Trizol (Gibco-BRL, Gaithersburg, Md.) was added to the cells. The cells were then extracted 1 time with 100% chloroform. The RNA in the aqueous phase was treated with 100% isopropyl alcohol and the resulting precipitate was pelleted at 12,000×rpm for 10 minutes. The resulting pellet containing RNA was resuspended in water containing 0.1% diethylpyrocarbonate (DEPC).

The RNA was then reverse transcribed into cDNA according to methods standard in the art using reverse transcriptase, oligo dT as a primer and a mixture of nucleotides.

B. Production of CD2, CD4 and Immunoglobulin cDNA cDNA encoding the extracellular domains of CD2 was produced by polymerase chain reaction (PCR) amplification using the following method. Human cDNA described in Section A was combined with CD2 sense primer (5' CGC TCT AGA ATG AGC TTT CCA TGT AAA TTT GTA 3'; SEQ ID NO:22) and CD2 anti-sense primer (5' TGT GGG CCC TCT GGG CTC GTC CAG ACC TTT CTC TGG 3'; SEQ ID NO:23). The mixture was amplified for 3 cycles at 94° C. (60 sec.), 50° C. (30 sec.), 72° C. (60 sec.) followed by 27 cycles at 94° C. (60 sec.), 55° C. (30 sec.), and 72° C. (60 sec.). A 10 minute 72° C. final elongation was then performed to produce amplified CD2 cDNA.

cDNA encoding the two amino terminal domains of CD4 was produced by PCR amplification using the following method. Human cDNA described in Section A was combined with CD4 sense primer (5' CGC TCT AGA ATG AAC CGG GGA GTC CCT 3'; SEQ ID NO:24) and CD4 anti-sense primer (5' GGG CCC TCT GGG CTC AGC TAG CAC CAC GAT GTC T 3'; SEQ ID NO:25). The mixture was then amplified as described above to produce amplified CD4 cDNA.

cDNA encoding the Fc domain of the 15.5.5 anti-class I (IgG2a isotype) monoclonal antibody was produced as follows. The cDNA produced from the 15.5.5 cell cDNA described in Section A was mixed with either a first IgG2a sense primer(CD2 sense primer: 5' CCA GAG AAA GGT CTG GAC GAG CCC AGA GGG CCC AC:3'; SEQ ID NO:26) or a second IgG2a sense primer (CD4 sense primer: 5' AGA CAT CGT GGT GCT AGC TGA GCC CAG AGG GCC C 3'; SEQ ID NO:27), and IgG2a anti-sense primer (5' GGC GAA TTC TTT ACC CGG AGT CCG GGA GAA GCT 3'; SEQ ID NO:28). The cDNAs were amplified using the conditions described in above to produce a first and a second IgG2a Fc domain cDNA.

C. Production of Chimeric Molecules

PCR amplification was then used to link cDNA encoding the extracellular domains of CD2 or CD4 to cDNA encoding the Fc domain of the 15.5.5 anti-class I monoclonal antibody (I.e., CD2-IgG2a fusion cDNA and CD4-IgG2a fusion cDNA).

CD2-IgG2a fusion cDNA was produced by combining cDNA encoding the extracellular domains of CD2 with cDNA encoding the Fc domain of 15.5.5 antibody produced using the CD2 sense primer. CD4-IgG2a fusion cDNA was produced by combining cDNA encoding the amino terminal domains of CD4 with cDNA encoding the Fc domain of 15.5.5 antibody produced using the CD4 sense primer. Both of the foregoing mixtures were amplified using the amplification conditions described in section B.

Example 2

This example describes the production of expression vectors encoding chimeric CD2:IgG2a or CD4:IgG2a fusion molecules.

Each of the CD2:IgG2a or CD4:IgG2a fusion cDNA described in Example 1 were purified on a 1.0% agarose gel and recovered by Geneclean Kit (BIO 101 Inc., LaJolla, Calif.). The gel purified CD2:IgG2a fragment was directly ligated into PCRII vector (Invitrogen, San Diego, Calif.). The CD4:IgG2a fragment was also directly ligated into the PCRII vector. The PCRII vector is a linear vector with poly T overhangs for direct ligation.

InvaF' *E. Coli* (obtained from Invitrogen) were then transformed with either pCD2:IgG2a or pCD4:IgG2a and the colonies were grown on LB plates containing about 100 mg/mL ampicillin. Resulting colonies were screened by PCR amplification using appropriate primers.

pCD2:IgG2a or pCD4:IgG2a plasmid was then isolated from bacterial colonies by propagating in liquid culture comprising LB broth and 50 mg/mL ampicillin and purifying the plasmid using methods standard in the art (see Sambrook et al., ibid.). Purified plasmid DNA was then digested with XbaI and EcoRI to yield a fragment of cDNA encoding a CD2-IgG2a fusion molecule or cDNA encoding a CD4-IgG2a fusion molecule. These fragments were then gel-purified as described above and separately ligated into the baculovirus transfer vector PVL 1393 (obtained from Pharmingen, San Diego, Calif.) which had previously been digested with XbaI and EcoRI, to form the expression vectors pVLCD2:IgG2a or pVLCD4:IgG2a. The expression vectors were then transformed into InvaF' *E. Coli*, selected as described above and frozen at −70° C. for later use.

Example 3

This Example shows that a CD4:anti-H-$2^d$, T lymphocyte veto molecule of the present invention, which is targeted to the class II MHC of allogeneic stimulator cells in a T cell proliferation assay, demonstrates significant and specific inhibition of CD4+ T-cell responses.

A transfectant secreting a soluble form of CD4 was obtained from K. Karjalainen (Basel Institute for Immunology). This material was purified by affinity chromatography and chemically (SPDP) cross-linked to the monoclonal antibody 14-4-4 which binds to certain class II MHC molecules (anti-H-$2^d$, but not anti-H-$2^b$) to form a hybrid antibody T lymphocyte veto molecule of the present invention.

Lymph node cells (50 or 200×10$^5$ per culture), which were enriched for CD4+ T-cells by two-step panning (purity >90% CD4$^+$ T-cells), were challenged with irradiated stimulator cells (200×105) in triplicate cultures (FIG. 1). These mixed lymphocyte cultures (MLCs) were set up in two combinations, C57BL/6 anti-BALB/c, where C57BL/6 cells are responders and BALB/c cells are stimulators (FIGS. 1A and 1B); and BALB/c anti-C57BL/6, where BALB/c cells are responders and C57BL/6 cells are stimulators (FIGS. 1C and 1D). Whereas in the first set of MLCs the hybrid antibody can bind to the stimulator cells (BALB/c H-$2^d$), in the second set it will not bind to the stimulator cells (C57BL/6 H-$2^b$), but will bind instead to the responder cells (BALB/c). Either the hybrid antibody, its non-linked components or medium only (nothing) was added to the MLCs. After 3 days, the cultures were pulsed with [$^3$H]-thymidine for 18 hours and then harvested.

Figure 1C:
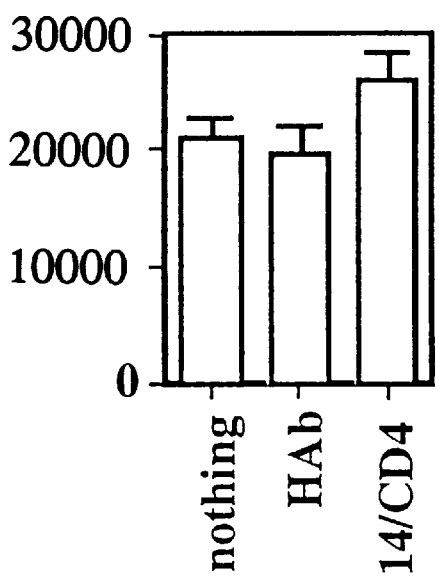
Figure 1D:
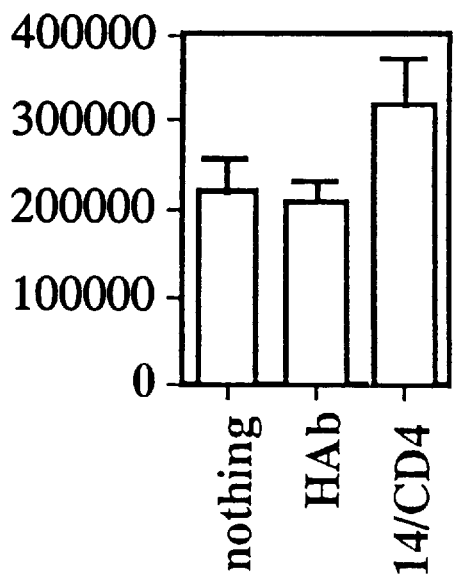

Inhibition of proliferation was only observed when the hybrid antibody bound to the stimulators (FIGS. 1A and 1B), but not when the antibody bound to the responders (FIGS. 1C and 1D). In addition, supplementing cultures with non-linked components of the hybrid antibody, soluble CD4 and 14-4-4, did not result in any reduction of the response. Therefore, in order to inhibit proliferation of allo-reactive CD4$^+$ T-cells, the CD4 molecule has to be linked to 14-4-4 in a hybrid antibody and the hybrid antibody has to bind to the stimulator cells. Thus, hybrid antibody-mediated 'veto' is effective and specific.

Figure 2:
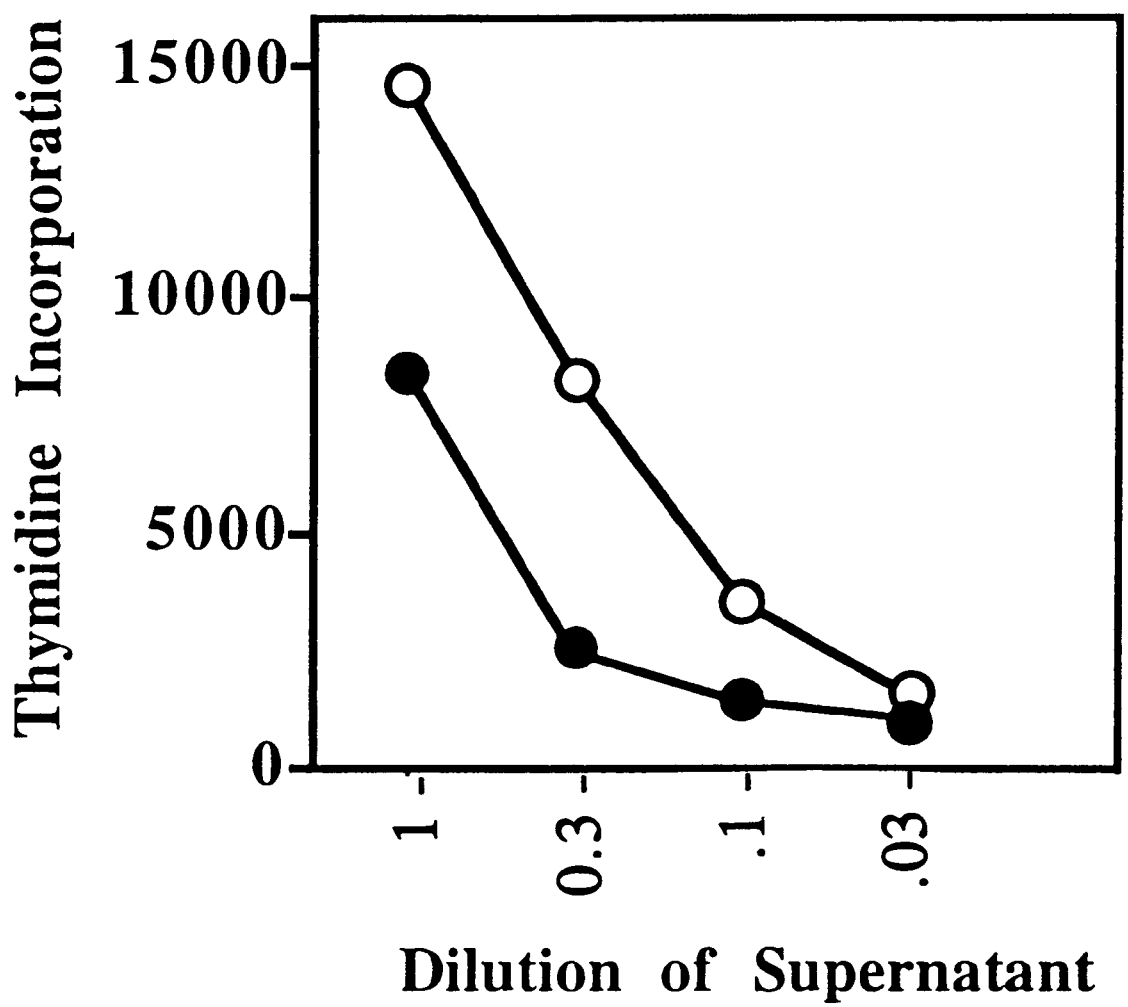
FIG. 2 shows the results of an experiment in which a T lymphocyte veto molecule of the present invention is capable of specifically inhibiting the production of IL-2 and IL-4 by CD4+ responder T cells.

To determine whether other T-cell functions besides proliferation were affected,. MLCs (C57BL/6 anti-BALB/c) were set up with CD4$^+$ T-cells. C57BL/6 CD4+ T-cell responders (200×10$^5$ per culture) were challenged with irradiated BALB/c stimulator cells (200×10$^5$ per culture). Either the hybrid antibody (shown in FIG. 2 as ●) or its non-linked components (shown in FIG. 2 as ○) were added. After 3 days supernatants were harvested and tested for the presence of IL-2 and IL-4 by adding the supernatants to HT-2 cells in different dilutions [neat (1), 30% (0.3), 10% (0.1) and 3% (0.3)]. After 18 hours HT-2 cells were pulsed with [3H]-thymidine. As shown in a representative experiment (FIG. 2), only the hybrid antibody was able to cause inhibition of IL-2/IL-4 production; its non-linked components failed to do so.

The foregoing experiment establishes the feasibility of this hybrid antibody inhibition by showing that 'veto' can be adapted for the inhibition of class II-reactive T-cells.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A T lymphocyte immunosuppression molecule comprising a chimeric molecule having a CD2 protein, wherein said CD2 protein is linked to a targeting immunoglobulin molecule that binds by its variable region to a molecule on the surface of a tissue graft cell that differentiates a host cell from said tissue graft cell.

2. The immunosuppression molecule of claim 1, wherein said protein is a CD2 protein that comprises the extracellular domains of a CD2 protein.

3. The immunosuppression molecule of claim 1, wherein said CD2 protein comprises an amino acid sequence SEQ ID NO:2.

4. The immunosuppression molecule of claim 1, wherein said protein is linked by a peptide bond to the constant region domain of said immunoglobulin molecule, to form a protein:Ig conjugated molecule.

5. The immunosuppression molecule of claim 4, wherein said immunoglobulin molecule of said protein:Ig conjugated molecule comprises a constant region domain of an IgG2a molecule.

6. The immunosuppression molecule of claim 4, wherein said protein:Ig conjugated molecule comprises an amino acid sequence comprising SEQ ID NO:18.

7. The immunosuppression molecule of claim 1, wherein said targeting immunoglobulin binds to a major histocompatibility molecule.

8. The veto molecule of claim 1, wherein said protein is linked to said targeting polypeptide by a chemically produced di-sulfide bond.

9. The immunosuppression molecule of claim 1, wherein said chimeric molecule can be secreted from a cell that produces said molecule.

10. A recombinant cell having: (1) a first recombinant molecule comprising a first nucleic acid molecule operatively linked to an expression vector, said first nucleic acid molecule having a sequence encoding a first CD2 protein; and (2) a second recombinant molecule comprising a second nucleic acid molecule operatively linked to an expression vector, said second nucleic acid molecule having a sequence encoding a second protein comprising a targeting immunoglobulin molecule selected from the group consisting of a targeting immunoglobulin molecule having a variable region that binds to a tissue graft cell surface molecule that differentiates a host cell from a tissue graft cell and a targeting immunoglobulin molecule having a variable region that selectively targets a molecule on the surface of a cell involved in an autoimmune response.

11. The recombinant cell of claim 10, wherein said first and second proteins are bound to the plasma membrane of said recombinant cell.

12. The recombinant cell of claim 10, wherein said recombinant cell is not capable of stimulating a T-cell response.

13. The recombinant cell of claim 10, wherein said recombinant cell is derived from a host cell selected from the group consisting of a fibroblast, a pluripotent progenitor cell, an epithelial cell, a neural cell, a T cell line and a B cell line.

14. The recombinant cell of claim 10, wherein said first nucleic acid molecule comprises a nucleic acid sequence that encodes an amino acid sequence SEQ ID NO:2.

15. A composition comprising: a T lymphocyte immunosuppression molecule comprising a recombinant chimeric molecule having a targeting immunoglobulin molecule selected from the group consisting of a targeting immunoglobulin molecule having a variable region that binds to a tissue graft cell surface molecule that differentiates a host cell from a tissue graft cell and a targeting immunoglobulin molecule having a variable region that selectively targets a molecule on the surface of a cell involved in an autoimmune response, wherein said targeting immunoglobulin molecule is linked to a CD2 protein; and a pharmaceutically acceptable carrier.

16. A method for producing a T lymphocyte immunosuppression molecule, comprising:

(a) providing a first protein comprising a CD2 protein;

(b) providing a second protein comprising a targeting immunoglobulin molecule selected from the group consisting of a targeting immunoglobulin molecule having a variable region that binds to a tissue graft cell surface molecule that differentiates a host cell from a tissue graft cell and a targeting immunoglobulin molecule having a variable region that selectively targets a molecule on the surface of a cell involved in an autoimmune response; and (c) linking said first protein to said second protein to form a chimeric molecule.

17. The method of claim 16, wherein said first protein is produced by culturing a cell transformed with a recombinant molecule comprising a nucleic acid molecule operatively linked to an expression vector, said nucleic acid molecule comprising a nucleic acid sequence that encodes an amino acid sequence SEQ ID NO:2.

18. The method of claim 16, wherein said second protein is produced by culturing a cell transformed with a recombinant molecule comprising a nucleic acid molecule operatively linked to an expression vector, said nucleic acid molecule comprising a nucleic acid sequence encoding an amino acid sequence derived from said immunoglobulin molecule.

19. The method of claim 16, wherein said step of linking comprises combining said first and second proteins and contacting said protein with a regent capable of creating di-sulfide bonds between said first and second proteins.

20. The method of claim 16, wherein said step of linking is performed using N-succinimidyl-3-1-(1-pyridyldthio)-propionate.

21. The method of claim 16, wherein said chimeric molecule is recovered from said first and second proteins that have not been linked.

22. The method of claim 16, wherein said chimeric molecule is recovered from said first and second proteins that have not been linked by a method selected from the group consisting of size separation chromatography, affinity chromatography, ion-exchange chromatography, reverse phase chromatography, chromatofocussing, hydroxyapatite adsorption and electrophoresis systems.

23. A T lymphocyte immunosuppression molecule comprising a chimeric molecule having a CD2 protein, wherein said protein is linked to a targeting immunoglobulin molecule that binds by its variable region to a molecule which selectively targets a cell involved in an autoimmune response.

24. The immunosuppression molecule of claim 23, wherein said protein comprises an amino acid sequence SEQ ID NO:2.

25. The immunosuppression molecule of claim 23, wherein said protein is linked by a peptide bond to the constant region domain of said immunoglobulin molecule, to form a protein:Ig conjugated molecule.

26. The immunosuppression molecule of claim 25, wherein said immunoglobulin molecule of said protein:Ig conjugated molecule comprises a constant region domain of an IgG2a molecule.

27. The immunosuppression molecule of claim 25, wherein said protein:Ig conjugated molecule comprises an amino acid sequence comprising SEQ ID NO:18.

28. The immunosuppression molecule of claim 23, wherein said targeting immunoglobulin molecule comprises an immunoglobulin that binds to a protein selected from the group consisting of a major histocompatibility molecule, asialoglycoprotein receptor, bile acid receptor, LMA surface target molecules, heart cell surface proteins, islets of Langerhans cell surface proteins, c-kit receptor and blood proteins.

29. The immunosuppression molecule of claim 23, wherein said protein is linked to said targeting polypeptide by a chemically produced di-sulfide bond.

30. The immunosuppression molecule of claim 23, wherein said chimeric molecule can be selected from a cell that produces said molecule.

31. A T lymphocyte immunosuppression molecule comprising a chimeric molecule having a CD2 protein, wherein said protein is linked to a monovalent targeting immunoglobulin molecule that binds by its variable region to a molecule on the surface of cell selected from the group consisting of a tissue graft cell that differentiates a host cell from said tissue graft cell, and a cell involved in an autoimmune response.

* * * * *

UNITED STATES PATENT AND TRADEMARK OFFICE
CERTIFICATE OF CORRECTION

PATENT NO. : 6,060,054
DATED : May 9, 2000
INVENTOR(S) : Staerz

It is certified that error appears in the above-identified patent and that said Letters Patent is hereby corrected as shown below:

Claim 8,
Line 1, delete "veto" and insert -- immunosuppression -- therefor;

Claim 19,
Line 10, delete "protein" and insert -- proteins -- therefor;
Line 10, delete "regent" and insert -- reagent -- therefor;

Claim 30,
Line 56, delete "selected" and insert -- secreted -- therefor.

Signed and Sealed this

Eleventh Day of September, 2001

Attest:

NICHOLAS P. GODICI
Attesting Officer   Acting Director of the United States Patent and Trademark Office

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
      (A) LENGTH: 138 amino acids
      (B) TYPE: amino acid
      (D) TOPOLOGY: linear (ii) MOLECULE TYPE: protein (xi) SEQUENCE DESCRIPTION: SEQ ID NO:1:

```
Asn Lys Val Val Leu Gly Lys Lys Gly Asp Thr Val Glu Leu Thr Cys
  1               5                  10                  15

Thr Ala Ser Gln Lys Lys Ser Ile Gln Phe His Trp Lys Asn Ser Asn
             20                  25                  30

Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile
            130                 135
```

(2) INFORMATION FOR SEQ ID NO:2:

(i) SEQUENCE CHARACTERISTICS:
      (A) LENGTH: 184 amino acids
      (B) TYPE: amino acid
      (D) TOPOLOGY: linear (ii) MOLECULE TYPE: protein (xi) SEQUENCE DESCRIPTION: SEQ ID NO:2:

```
Lys Glu Ile Thr Asn Ala Leu Glu Thr Trp Gly Ala Leu Gly Gln Asp
  1               5                  10                  15

Ile Asn Leu Asp Ile Pro Ser Phe Gln Met Ser Asp Asp Ile Asp Asp
             20                  25                  30

Ile Lys Trp Glu Lys Thr Ser Asp Lys Lys Lys Ile Ala Gln Phe Arg
         35                  40                  45

Lys Glu Lys Glu Thr Phe Lys Glu Lys Asp Thr Tyr Lys Leu Phe Lys
 50                  55                  60

Asn Gly Thr Leu Lys Ile Lys His Leu Lys Thr Asp Asp Gln Asp Ile
 65                  70                  75                  80

Tyr Lys Val Ser Ile Tyr Asp Thr Lys Gly Lys Asn Val Leu Glu Lys
                 85                  90                  95

Ile Phe Asp Leu Lys Ile Gln Glu Arg Val Ser Lys Pro Lys Ile Ser
                100                 105                 110
```

```
Trp Thr Cys Ile Asn Thr Thr Leu Thr Cys Glu Val Met Asn Gly Thr
            115                 120                 125

Asp Pro Glu Leu Asn Leu Tyr Gln Asp Gly Lys His Leu Lys Leu Ser
130                 135                 140

Gln Arg Val Ile Thr His Lys Trp Ile Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu
            180
```

(2) INFORMATION FOR SEQ ID NO:3:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:3:

```
Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
                100                 105                 110

Thr Ile Ile His Val Lys Gly Lys His Leu Cys Pro Ser Pro Leu Phe
            115                 120                 125

Pro Gly Pro Ser Lys Pro
            130
```

(2) INFORMATION FOR SEQ ID NO:4:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:4:

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
50                  55                  60

Ile Cys Thr Gly Thr Ser Ser Gly Asn Gln Val Asn Leu Thr Ile Gln
```

```
                      65                  70                  75                  80

Gly Leu Arg Ala Met Asp Thr Gly Leu Tyr Ile Cys Lys Val Glu Leu
                     85                  90                  95

Met Tyr Pro Pro Pro Tyr Tyr Leu Gly Ile Gly Asn Gly Ala Gln Ile
                100                 105                 110

Tyr Val Ile Asp Pro Glu Pro Cys Pro Asp Ser Asp
            115                 120
```

(2) INFORMATION FOR SEQ ID NO:5:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:5:

```
Pro Pro Glu Lys Lys Glu Leu Arg Lys Val Ala His Leu Thr Gly Lys
1                   5                  10                  15

Ser Asn Ser Arg Ser Met Pro Leu Glu Trp Glu Asp Thr Tyr Gly Ile
                 20                  25                  30

Val Leu Leu Ser Gly Val Lys Tyr Lys Lys Gly Gly Leu Val Ile Asn
             35                  40                  45

Glu Thr Gly Leu Tyr Phe Val Tyr Ser Lys Val Tyr Phe Arg Gly Gln
 50                  55                  60

Ser Cys Asn Asn Leu Pro Leu Ser His Lys Val Tyr Met Arg Asn Ser
65                  70                  75                  80

Lys Tyr Pro Gln Asp Leu Val Met Met Glu Gly Lys Met Met Ser Tyr
                 85                  90                  95

Cys Thr Thr Gly Gln Met Trp Ala Arg Ser Ser Tyr Lys Gly Ala Val
                100                 105                 110

Phe Asn Leu Thr Ser Ala Asp His Leu Tyr Val Asn Val Ser Glu Leu
            115                 120                 125

Ser Leu Val Asn Phe Glu Glu Ser Gln Thr Phe Phe Gly Leu Tyr Lys
    130                 135                 140

Leu
145
```

(2) INFORMATION FOR SEQ ID NO:6:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:6:

```
Arg Leu Ser Trp Tyr Asp Pro Asp Phe Gln Ala Arg Leu Thr Arg Ser
1                   5                  10                  15

Asn Ser Lys Cys Gln Gly Gln Leu Glu Val Tyr Leu Lys Asp Gly Trp
                 20                  25                  30

His Met Val Cys Ser Gln Ser Trp Gly Arg Ser Ser Lys Gln Trp Glu
             35                  40                  45

Asp Pro Ser Gln Ala Ser Lys Val Cys Gln Arg Leu Asn Cys Gly Val
 50                  55                  60

Pro Leu Ser Leu Gly Pro Phe Leu Val Thr Tyr Thr Pro Gln Ser Ser
65                  70                  75                  80
```

```
Ile Ile Cys Tyr Gly Gln Leu Gly Ser Phe Ser Asn Cys Ser His Ser
                85                  90                  95

Arg Asn Asp Met Cys His Ser Leu Gly Leu Thr Cys Leu Glu Pro Gln
            100                 105                 110

Lys Thr Thr Pro Pro Thr Thr Ile Ile Pro Pro Thr Thr Thr Pro
            115                 120                 125

Glu Pro Thr Ala Pro Pro Arg Leu Gln Leu Val Ala Gln Ser Gly Gly
            130                 135                 140

Gln His Cys Ala Gly Val Val Glu Phe Tyr Ser Gly Ser Leu Gly Gly
145                 150                 155                 160

Thr Ile Ser Tyr Glu Ala Gln Asp Lys Thr Gln Asp Leu Glu Asn Phe
                165                 170                 175

Leu Cys Asn Asn Leu Gln Cys Gly Ser Phe Leu Lys His Leu Pro Glu
                180                 185                 190

Thr Glu Ala Gly Arg Ala Gln Asp Pro Gly Glu Pro Arg Glu His Gln
                195                 200                 205

Pro Leu Pro Ile Gln Trp Lys Ile Gln Asn Ser Ser Cys Thr Ser Leu
    210                 215                 220

Glu His Cys Phe Arg Lys Ile Lys Pro Gln Lys Ser Gly Arg Val Leu
225                 230                 235                 240

Ala Leu Leu Cys Ser Gly Phe Gln Pro Lys Val Gln Ser Arg Leu Val
                245                 250                 255

Gly Gly Ser Ser Ile Cys Glu Gly Thr Val Glu Val Arg Gln Gly Ala
                260                 265                 270

Gln Trp Ala Ala Leu Cys Asp Ser Ser Ala Arg Ser Ser Leu Arg
    275                 280                 285

Trp Glu Glu Val Cys Arg Glu Gln Gln Cys Gly Ser Val Asn Ser Tyr
    290                 295                 300

Arg Val Leu Asp Ala Gly Asp Pro Thr Ser Arg Gly Leu Phe Cys Pro
305                 310                 315                 320

His Gln Lys Leu Ser Gln Cys His Glu Leu Trp Glu Arg Asn Ser Tyr
                325                 330                 335

Cys Lys Lys Val Phe Val Thr Cys Gln Asp Pro Asn Pro
                340                 345
```

(2) INFORMATION FOR SEQ ID NO:7:

(i) SEQUENCE CHARACTERISTICS:
        (A) LENGTH: 154 amino acids
        (B) TYPE: amino acid
        (D) TOPOLOGY: linear (ii) MOLECULE TYPE: protein (xi) SEQUENCE DESCRIPTION: SEQ ID NO:7:

```
Ala Gln Glu Val Gln Gln Ser Pro His Cys Thr Thr Val Pro Gly Ala
1               5                   10                  15

Ser Val Asn Ile Thr Cys Ser Ser Gly Gly Leu Arg Gly Ile Tyr
                20                  25                  30

Leu Pro Gln Leu Gly Pro Gln Pro Gln Asp Ile Ile Tyr Tyr Glu Asp
            35                  40                  45

Gly Val Val Pro Thr Thr Asp Arg Arg Phe Arg Gly Arg Ile Asp Phe
    50                  55                  60

Ser Gly Ser Gln Asp Asn Leu Thr Ile Thr Met His Arg Leu Gln Leu
65                  70                  75                  80
```

```
Ser Asp Thr Gly Thr Tyr Thr Cys Gln Ala Ile Thr Glu Val Asn Val
                85                  90                  95

Tyr Gly Ser Gly Thr Leu Val Leu Val Thr Glu Glu Gln Ser Gln Gly
               100                 105                 110

Trp His Arg Cys Ser Asp Ala Pro Pro Arg Ala Ser Ala Leu Pro Ala
               115                 120                 125

Pro Pro Thr Gly Ser Ala Leu Pro Asp Pro Gln Thr Ala Ser Ala Leu
        130                 135                 140

Pro Asp Pro Pro Ala Ala Ser Ala Leu Pro
145                 150
```

(2) INFORMATION FOR SEQ ID NO:8:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO:8:

```
His Lys Asp Glu Val Ile Lys Glu Val Gln Glu Phe Tyr Lys Asp Thr
1               5                   10                  15

Tyr Asn Lys Leu Lys Thr Lys Asp Glu Pro Gln Arg Glu Thr Leu Lys
                20                  25                  30

Ala Ile His Tyr Ala Leu Asn Cys Cys Gly Leu Ala Gly Val Ala
                35                  40                  45

Gln Phe Ile Ser Asp Ile Cys Pro Lys Lys Asp Val Leu Glu Thr Phe
        50                  55                  60

Thr Val Lys Ser Cys Pro Asp Ile Lys Glu Val Phe Asp Asn Lys
65                  70                  75
```

(2) INFORMATION FOR SEQ ID NO:9:

(i) SEQUENCE CHARACTERISTICS:
        (A) LENGTH: 1065 amino acids
        (B) TYPE: amino acid
        (D) TOPOLOGY: linear (ii) MOLECULE TYPE: protein (xi) SEQUENCE DESCRIPTION: SEQ ID NO:9:

```
Tyr Asn Leu Asp Val Arg Gly Ala Arg Ser Phe Ser Pro Pro Arg Ala
1               5                   10                  15

Gly Arg His Phe Gly Tyr Arg Val Leu Gln Val Gly Asn Gly Val Ile
                20                  25                  30

Val Gly Ala Pro Gly Glu Gly Asn Ser Thr Gly Ser Leu Tyr Gln Cys
            35                  40                  45

Gln Ser Gly Thr Gly His Cys Leu Pro Val Thr Leu Arg Gly Ser Asn
        50                  55                  60

Tyr Thr Ser Lys Tyr Leu Gly Met Thr Leu Ala Thr Asp Pro Thr Asp
65                  70                  75                  80

Gly Ser Ile Leu Ala Cys Asp Pro Gly Leu Ser Arg Thr Cys Asp Gln
                85                  90                  95

Asn Thr Tyr Leu Ser Gly Leu Cys Tyr Leu Phe Arg Gln Asn Leu Gln
                100                 105                 110

Gly Pro Met Leu Gln Gly Arg Pro Gly Phe Gln Glu Cys Ile Lys Gly
            115                 120                 125

Asn Val Asp Leu Val Phe Leu Phe Asp Gly Ser Met Ser Leu Gln Pro
```

```
            130                 135                 140
Asp Glu Phe Gln Lys Ile Leu Asp Phe Met Lys Asp Val Met Lys Lys
145                 150                 155                 160
Leu Ser Asn Thr Ser Tyr Gln Phe Ala Ala Val Gln Phe Ser Thr Ser
                    165                 170                 175
Tyr Lys Thr Glu Phe Asp Phe Ser Asp Tyr Val Lys Trp Lys Asp Pro
                180                 185                 190
Asp Ala Leu Leu Lys His Val Lys His Met Leu Leu Leu Thr Asn Thr
            195                 200                 205
Phe Gly Ala Ile Asn Tyr Val Ala Thr Glu Val Phe Arg Glu Glu Leu
210                 215                 220
Gly Ala Arg Pro Asp Ala Thr Lys Val Leu Ile Ile Thr Asp Gly
225                 230                 235                 240
Glu Ala Thr Asp Ser Gly Asn Ile Asp Ala Lys Asp Ile Ile Arg
                245                 250                 255
Tyr Ile Ile Gly Ile Gly Lys His Phe Gln Thr Lys Glu Ser Gln Glu
                260                 265                 270
Thr Leu His Lys Phe Ala Ser Lys Pro Ala Ser Glu Phe Val Lys Ile
            275                 280                 285
Leu Asp Thr Phe Glu Lys Leu Lys Asp Leu Phe Thr Glu Leu Gln Lys
290                 295                 300
Lys Ile Tyr Val Ile Glu Gly Thr Ser Lys Gln Asp Leu Thr Ser Phe
305                 310                 315                 320
Asn Met Glu Leu Ser Ser Ser Gly Ile Ser Ala Asp Leu Ser Arg Gly
                325                 330                 335
His Ala Val Val Gly Ala Val Gly Ala Lys Asp Trp Ala Gly Gly Phe
                340                 345                 350
Leu Asp Leu Lys Ala Asp Leu Gln Asp Asp Thr Phe Ile Gly Asn Glu
            355                 360                 365
Pro Leu Thr Pro Glu Val Arg Ala Gly Tyr Leu Gly Tyr Thr Val Thr
            370                 375                 380
Trp Leu Pro Ser Arg Gln Lys Thr Ser Leu Leu Ala Ser Gly Ala Pro
385                 390                 395                 400
Arg Tyr Gln His Met Gly Arg Val Leu Leu Phe Gln Glu Pro Gln Gly
                405                 410                 415
Gly Gly His Trp Ser Gln Val Gln Thr Ile His Gly Thr Gln Ile Gly
                420                 425                 430
Ser Tyr Phe Gly Gly Glu Leu Cys Gly Val Asp Val Asp Gln Asp Gly
            435                 440                 445
Glu Thr Glu Leu Leu Leu Ile Gly Ala Pro Leu Phe Tyr Gly Glu
            450                 455                 460
Gln Arg Gly Gly Arg Val Phe Ile Tyr Gln Arg Arg Gln Leu Gly Phe
465                 470                 475                 480
Glu Glu Val Ser Glu Leu Gln Gly Asp Pro Gly Tyr Pro Leu Gly Arg
                485                 490                 495
Phe Gly Glu Ala Ile Thr Ala Leu Thr Asp Ile Asn Gly Asp Gly Leu
                500                 505                 510
Val Asp Val Ala Val Gly Ala Pro Leu Glu Glu Gln Gly Ala Val Tyr
            515                 520                 525
Ile Phe Asn Gly Arg His Gly Gly Leu Ser Pro Gln Pro Ser Gln Arg
            530                 535                 540
Ile Glu Gly Thr Gln Val Leu Ser Gly Ile Gln Trp Phe Gly Arg Ser
545                 550                 555                 560
```

-continued

```
Ile His Gly Val Lys Asp Leu Glu Gly Asp Gly Leu Ala Asp Val Ala
                565                 570                 575
Val Gly Ala Glu Ser Gln Met Ile Val Leu Ser Ser Arg Pro Val Val
            580                 585                 590
Asp Met Val Thr Leu Met Ser Phe Ser Pro Ala Glu Ile Pro Val His
            595                 600                 605
Glu Val Glu Cys Ser Tyr Ser Thr Ser Asn Lys Met Lys Glu Gly Val
            610                 615                 620
Asn Ile Thr Ile Cys Phe Gln Ile Lys Ser Leu Tyr Pro Gln Phe Gln
625                 630                 635                 640
Gly Arg Leu Val Ala Asn Leu Thr Tyr Thr Leu Gln Leu Asp Gly His
                645                 650                 655
Arg Thr Arg Arg Arg Gly Leu Phe Pro Gly Gly Arg His Glu Leu Arg
                660                 665                 670
Arg Asn Ile Ala Val Thr Thr Ser Met Ser Cys Thr Asp Phe Ser Phe
            675                 680                 685
His Phe Pro Val Cys Val Gln Asp Leu Ile Ser Pro Ile Asn Val Ser
            690                 695                 700
Leu Asn Phe Ser Leu Trp Glu Glu Gly Thr Pro Arg Asp Gln Arg
705                 710                 715                 720
Ala Gln Gly Lys Asp Ile Pro Pro Ile Leu Arg Pro Ser Leu His Ser
                725                 730                 735
Glu Thr Trp Glu Ile Pro Phe Glu Lys Asn Cys Gly Glu Asp Lys Lys
            740                 745                 750
Cys Glu Ala Asn Leu Arg Val Ser Phe Ser Pro Ala Arg Ser Arg Ala
            755                 760                 765
Leu Arg Leu Thr Ala Phe Ala Ser Leu Ser Val Glu Leu Ser Leu Ser
770                 775                 780
Asn Leu Glu Glu Asp Ala Tyr Trp Val Gln Leu Asp Leu His Phe Pro
785                 790                 795                 800
Pro Gly Leu Ser Phe Arg Lys Val Glu Met Leu Lys Pro His Ser Gln
                805                 810                 815
Ile Pro Val Ser Cys Glu Glu Leu Pro Glu Glu Ser Arg Leu Leu Ser
            820                 825                 830
Arg Ala Leu Ser Cys Asn Val Ser Ser Pro Ile Phe Lys Ala Gly His
            835                 840                 845
Ser Val Ala Leu Gln Met Asn Phe Asn Thr Leu Val Asn Ser Ser Trp
            850                 855                 860
Gly Asp Ser Val Glu Leu His Ala Asn Val Thr Cys Asn Asn Glu Asp
865                 870                 875                 880
Ser Asp Leu Leu Glu Asp Asn Ser Ala Thr Thr Ile Ile Pro Ile Leu
                885                 890                 895
Tyr Pro Ile Asn Ile Leu Ile Gln Asp Gln Glu Asp Ser Thr Leu Tyr
                900                 905                 910
Val Ser Phe Thr Pro Lys Gly Pro Lys Ile His Gln Val Lys His Met
            915                 920                 925
Tyr Gln Val Arg Ile Gln Pro Ser Ile His Asp His Asn Ile Pro Thr
            930                 935                 940
Leu Glu Ala Val Val Gly Val Pro Gln Pro Pro Ser Glu Gly Pro Ile
945                 950                 955                 960
Thr His Gln Trp Ser Val Gln Met Glu Pro Pro Tyr Pro Cys His Tyr
                965                 970                 975
```

-continued

```
Glu Asp Leu Glu Arg Leu Pro Asp Ala Ala Glu Pro Cys Leu Pro Gly
            980                 985                 990
Ala Leu Phe Arg Cys Pro Val Val Phe Arg Gln Glu Ile Leu Val Gln
            995                1000                1005
Val Ile Gly Thr Leu Glu Leu Val Gly Glu Ile Glu Ala Ser Ser Met
           1010                1015                1020
Phe Ser Leu Cys Ser Ser Leu Ser Ile Ser Phe Asn Ser Ser Lys His
1025                1030                1035                1040
Phe His Leu Tyr Gly Ser Asn Ala Ser Leu Ala Gln Val Val Met Lys
                    1045                1050                1055
Val Asp Val Val Tyr Glu Lys Gln Met
                    1060                1065

(2) INFORMATION FOR SEQ ID NO:10:

(i) SEQUENCE CHARACTERISTICS:
        (A) LENGTH: 676 amino acids
        (B) TYPE: amino acid
        (D) TOPOLOGY: linear (ii) MOLECULE TYPE: protein xi) SEQUENCE DESCRIPTION: SEQ ID NO:10:

Gln Glu Cys Thr Lys Phe Lys Val Ser Ser Cys Arg Glu Cys Ile Glu
1               5                  10                  15
Ser Gly Pro Gly Cys Thr Trp Cys Gln Lys Leu Asn Phe Thr Gly Pro
                20                  25                  30
Gly Asp Pro Asp Ser Ile Arg Cys Asp Thr Arg Pro Gln Leu Leu Met
            35                  40                  45
Arg Gly Cys Ala Ala Asp Asp Ile Met Asp Pro Thr Ser Leu Ala Glu
         50                  55                  60
Thr Gln Glu Asp His Asn Gly Gly Gln Lys Gln Leu Ser Pro Gln Lys
65                  70                  75                  80
Val Thr Leu Tyr Leu Arg Pro Gly Gln Ala Ala Ala Phe Asn Val Thr
                85                  90                  95
Phe Arg Arg Ala Lys Gly Tyr Pro Ile Asp Leu Tyr Tyr Leu Met Asp
                100                 105                 110
Leu Ser Tyr Ser Met Leu Asp Asp Leu Arg Asn Val Lys Lys Leu Gly
            115                 120                 125
Gly Asp Leu Leu Arg Ala Leu Asn Glu Ile Thr Glu Ser Gly Arg Ile
        130                 135                 140
Gly Phe Gly Ser Phe Val Asp Lys Thr Val Leu Pro Phe Val Asn Thr
145                 150                 155                 160
His Pro Asp Lys Leu Arg Asn Pro Cys Pro Asn Lys Glu Lys Glu Cys
                165                 170                 175
Gln Pro Pro Phe Ala Phe Arg His Val Leu Lys Leu Thr Asn Asn Ser
                180                 185                 190
Asn Gln Phe Gln Thr Glu Val Gly Lys Gln Leu Ile Ser Gly Asn Leu
            195                 200                 205
Asp Ala Pro Glu Gly Gly Leu Asp Ala Met Met Gln Val Ala Ala Cys
        210                 215                 220
Pro Glu Glu Ile Gly Asn Arg Asn Val Thr Arg Leu Leu Val Phe Ala
225                 230                 235                 240
Thr Asp Asp Gly Phe His Phe Ala Gly Asp Gly Lys Leu Gly Ala Ile
                245                 250                 255
Leu Thr Pro Asn Asp Gly Arg Cys His Leu Glu Asp Asn Leu Tyr Lys
```

-continued

```
                260                 265                 270
Arg Ser Asn Glu Phe Asp Tyr Pro Ser Val Gly Gln Leu Ala His Lys
                275                 280                 285
Leu Ala Glu Asn Asn Ile Gln Pro Ile Phe Ala Val Thr Ser Arg Met
                290                 295                 300
Val Lys Thr Tyr Glu Lys Leu Thr Glu Ile Ile Pro Lys Ser Ala Val
305                 310                 315                 320
Gly Glu Leu Ser Glu Asp Ser Ser Asn Val Val His Leu Ile Lys Asn
                325                 330                 335
Ala Tyr Asn Lys Leu Ser Ser Arg Val Phe Leu Asp His Asn Ala Leu
                340                 345                 350
Pro Asp Thr Leu Lys Val Thr Tyr Asp Ser Phe Cys Ser Asn Gly Val
                355                 360                 365
Thr His Arg Asn Gln Pro Arg Gly Asp Cys Asp Gly Val Gln Ile Asn
                370                 375                 380
Val Pro Ile Thr Phe Gln Val Lys Val Thr Ala Thr Glu Cys Ile Gln
385                 390                 395                 400
Glu Gln Ser Phe Val Ile Arg Ala Leu Gly Phe Thr Asp Ile Val Thr
                405                 410                 415
Val Gln Val Leu Pro Gln Cys Glu Cys Arg Cys Arg Asp Gln Ser Arg
                420                 425                 430
Asp Arg Ser Leu Cys His Gly Lys Gly Phe Leu Glu Cys Gly Ile Cys
                435                 440                 445
Arg Cys Asp Thr Gln Tyr Ile Gly Lys Asn Cys Glu Cys Gln Thr Gln
                450                 455                 460
Gly Arg Ser Ser Gln Glu Leu Glu Gly Ser Cys Arg Lys Asp Asn Asn
465                 470                 475                 480
Ser Ile Ile Cys Ser Gly Leu Gly Asp Cys Val Cys Gly Gln Cys Leu
                485                 490                 495
Cys His Thr Ser Asp Val Pro Gly Lys Leu Ile Tyr Gly Gln Tyr Cys
                500                 505                 510
Glu Cys Asp Thr Ile Asn Cys Glu Arg Tyr Asn Gly Gln Val Cys Gly
                515                 520                 525
Gly Pro Gly Arg Gly Leu Cys Phe Cys Gly Lys Cys Arg Cys His Pro
                530                 535                 540
Gly Phe Glu Gly Ser Ala Cys Gln Cys Glu Arg Thr Thr Glu Gly Cys
545                 550                 555                 560
Leu Asn Pro Arg Arg Val Glu Cys Ser Gly Arg Gly Arg Cys Arg Cys
                565                 570                 575
Asn Val Cys Glu Cys His Ser Gly Tyr Gln Leu Pro Leu Cys Gln Glu
                580                 585                 590
Cys Pro Gly Cys Pro Ser Cys Gly Lys Tyr Ile Ser Cys Ala Glu Cys
                595                 600                 605
Leu Lys Phe Glu Lys Gly Pro Phe Gly Lys Asn Cys Ser Ala Ala Cys
                610                 615                 620
Pro Gly Leu Gln Leu Ser Asn Asn Pro Val Lys Gly Arg Thr Cys Lys
625                 630                 635                 640
Glu Arg Asp Ser Glu Gly Cys Trp Val Ala Tyr Thr Leu Glu Gln Gln
                645                 650                 655
Asp Gly Met Asp Arg Tyr Leu Ile Tyr Val Asp Glu Ser Arg Glu Cys
                660                 665                 670
Val Ala Gly Pro
                675
```

(2) INFORMATION FOR SEQ ID NO:11:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO:11:

```
Thr Pro Ala Pro Lys Ser Cys Pro Glu Arg His Tyr Trp Ala Gln Gly
 1               5                  10                  15

Lys Leu Cys Cys Gln Met Cys Glu Pro Gly Thr Phe Leu Val Lys Asp
            20                  25                  30

Cys Gln His Arg Lys Ala Ala Gln Cys Asp Pro Cys Ile Pro Gly Val
        35                  40                  45

Ser Phe Ser Asp Pro His His Thr Arg Pro His Cys Glu Ser Cys Arg
    50                  55                  60

His Cys Asn Ser Gly Leu Leu Val Arg Asn Cys Ile Thr Ala Asn Ala
65                  70                  75                  80

Glu Cys Ala Cys Arg Asn Gly Trp Gln Cys Arg Asp Lys Glu Cys Thr
                85                  90                  95

Glu Cys Asp Pro Leu Pro Asn Pro Ser Leu Thr Ala Arg Ser Ser Gln
            100                 105                 110

Ala Leu Ser Pro His Pro Gln Pro Thr His Leu Pro Tyr Val Ser Glu
        115                 120                 125

Met Leu Glu Ala Ser Thr Ala Gly His Met Gln Thr Leu Ala Asp Phe
    130                 135                 140

Arg Gln Leu Pro Ala Arg Thr Leu Ser Thr His Trp Pro Pro Gln Arg
145                 150                 155                 160

Ser Leu Cys Ser Ser Asp Phe Ile Arg
                165
```

(2) INFORMATION FOR SEQ ID NO:12:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Ala Leu Gly Ser Thr Thr Ala Val Gln Thr Pro Thr Ser Gly Glu
 1               5                  10                  15

Pro Leu Val Ser Thr Ser Glu Pro Leu Ser Ser Lys Met Tyr Thr Thr
            20                  25                  30

Ser Ile Thr Ser Asp Pro Lys Ala Asp Ser Thr Gly Asp Gln Thr Ser
        35                  40                  45

Ala Leu Pro Pro Ser Thr Ser Ile Asn Glu Gly Ser Pro Leu Trp Thr
    50                  55                  60

Ser Ile Gly Ala Ser Thr Gly Ser Pro Leu Pro Glu Pro Thr Thr Tyr
65                  70                  75                  80

Gln Glu Val Ser Ile Lys Met Ser Ser Val Pro Gln Glu Thr Pro His
                85                  90                  95

Ala Thr Ser His Pro Ala Val Pro Ile Thr Ala Asn Ser Leu Gly Ser
            100                 105                 110
```

-continued

```
His Thr Val Thr Gly Gly Thr Ile Thr Thr Asn Ser Pro Glu Thr Ser
        115                 120                 125

Ser Arg Thr Ser Gly Ala Pro Val Thr Thr Ala Ala Ser Ser Leu Glu
    130                 135                 140

Thr Ser Arg Gly Thr Ser Gly Pro Pro Leu Thr Met Ala Thr Val Ser
145                 150                 155                 160

Leu Glu Thr Ser Lys Gly Thr Ser Gly Pro Pro Val Thr Met Ala Thr
                165                 170                 175

Asp Ser Leu Glu Thr Ser Thr Gly Thr Thr Gly Pro Pro Val Thr Met
            180                 185                 190

Thr Thr Gly Ser Leu Glu Pro Ser Ser Gly Ala Ser Gly Pro Gln Val
        195                 200                 205

Ser Ser Val Lys Leu Ser Thr Met Met Ser Pro Thr Thr Ser Thr Asn
    210                 215                 220

Ala Ser Thr Val Pro Phe Asn Pro Asp Glu Asn Ser Arg Gly Met Leu
225                 230                 235                 240

Pro Val Ala Val Leu Val Ala Leu Leu Ala Val Ile Val Leu Val Ala
                245                 250                 255

Leu Leu Leu Leu Trp Arg Arg Arg Gln Lys Arg Arg Thr Gly Ala Leu
            260                 265                 270

Val Leu Ser Arg Gly Gly Lys Arg Asn Gly Val Val Asp Ala Trp Ala
        275                 280                 285

Gly Pro Ala Gln Val Pro Glu Glu Gly Ala Val Thr Val Thr Val Gly
    290                 295                 300

Gly Ser Gly Gly Asp Lys Gly Ser Gly Phe Pro Asp Gly Glu Gly
305                 310                 315
```

(2) INFORMATION FOR SEQ ID NO:13:

(i) SEQUENCE CHARACTERISTICS:
        (A) LENGTH: 553 amino acids
        (B) TYPE: amino acid
        (D) TOPOLOGY: linear (ii) MOLECULE TYPE: protein (ix) FEATURE:
        (A) NAME/KEY: Domain
        (B) LOCATION: 1..74
        (D) OTHER INFORMATION: /note= "product of exon A"

(ix) FEATURE:
        (A) NAME/KEY: Domain
        (B) LOCATION: 75..122
        (D) OTHER INFORMATION: /note= "product of exon B"

(ix) FEATURE:
        (A) NAME/KEY: Domain
        (B) LOCATION: 123..170
        (D) OTHER INFORMATION: /note= "product of exon C"

(xi) SEQUENCE DESCRIPTION: SEQ ID NO:13:

```
Gln Ser Pro Thr Pro Ser Pro Thr Gly Leu Thr Thr Ala Lys Met Pro
1               5                   10                  15

Ser Trp Pro Leu Ser Ser Asp Pro Leu Pro Thr His Thr Thr Ala Phe
            20                  25                  30

Ser Pro Ala Ser Thr Phe Glu Arg Glu Asn Asp Phe Ser Glu Thr Thr
        35                  40                  45

Thr Ser Leu Ser Pro Asp Asn Thr Ser Thr Gln Val Ser Pro Asp Ser
    50                  55                  60

Leu Asp Asn Ala Ser Ala Phe Asn Thr Thr Gly Val Ser Ser Val Gln
```

```
65                    70                   75                   80
Thr Pro His Leu Pro Thr His Ala Asp Ser Gln Thr Pro Ser Ala Gly
                85                   90                   95
Thr Asp Thr Gln Thr Phe Ser Gly Ser Ala Ala Asx Ala Lys Leu Asn
               100                  105                  110
Pro Thr Pro Gly Ser Asn Ala Ile Ser Asp Val Pro Gly Glu Arg Ser
               115                  120                  125
Thr Ala Ser Thr Phe Pro Thr Asp Pro Val Ser Pro Leu Thr Thr Thr
           130                  135                  140
Leu Ser Leu Ala His His Ser Ser Ala Ala Leu Pro Ala Arg Thr Ser
145                  150                  155                  160
Asn Thr Thr Ile Thr Ala Asn Thr Ser Asp Ala Tyr Leu Asn Ala Ser
               165                  170                  175
Glu Thr Thr Thr Leu Ser Pro Ser Gly Ser Ala Val Ile Ser Thr Thr
           180                  185                  190
Thr Ile Ser Thr Thr Pro Ser Lys Pro Thr Cys Asp Glu Lys Tyr Ala
           195                  200                  205
Asn Ile Thr Val Asp Tyr Leu Tyr Asn Lys Glu Thr Lys Leu Phe Thr
210                  215                  220
Ala Lys Leu Asn Val Asn Glu Asn Val Glu Cys Gly Asn Asn Thr Cys
225                  230                  235                  240
Thr Asn Asn Glu Val His Asn Leu Thr Glu Cys Lys Asn Ala Ser Val
               245                  250                  255
Ser Ile Ser His Asn Ser Cys Thr Ala Pro Asp Lys Thr Leu Ile Leu
               260                  265                  270
Asp Val Pro Pro Gly Val Glu Lys Phe Gln Leu His Asp Cys Thr Gln
           275                  280                  285
Val Glu Lys Ala Asp Thr Thr Ile Cys Leu Lys Trp Lys Asn Ile Glu
           290                  295                  300
Thr Phe Thr Cys Asp Thr Gln Asn Ile Thr Tyr Arg Phe Gln Cys Gly
305                  310                  315                  320
Asn Met Ile Phe Asp Asn Lys Glu Ile Lys Leu Glu Asn Leu Glu Pro
               325                  330                  335
Glu His Glu Tyr Lys Cys Asp Ser Glu Ile Leu Tyr Asn Asn His Lys
               340                  345                  350
Phe Thr Asn Ala Ser Lys Ile Ile Lys Thr Asp Phe Gly Ser Pro Gly
               355                  360                  365
Glu Pro Gln Ile Ile Phe Cys Arg Ser Glu Ala Ala His Gln Gly Val
           370                  375                  380
Ile Thr Trp Asn Pro Pro Gln Arg Ser Phe His Asn Phe Thr Leu Cys
385                  390                  395                  400
Tyr Ile Lys Glu Thr Glu Lys Asp Cys Leu Asn Leu Asp Lys Asn Leu
               405                  410                  415
Ile Lys Tyr Asp Leu Gln Asn Leu Lys Pro Tyr Thr Lys Tyr Val Leu
           420                  425                  430
Ser Leu His Ala Tyr Ile Ile Ala Lys Val Gln Arg Asn Gly Ser Ala
           435                  440                  445
Ala Met Cys His Phe Thr Thr Lys Ser Ala Pro Pro Ser Gln Val Trp
450                  455                  460
Asn Met Thr Val Ser Met Thr Ser Asp Asn Ser Met His Val Lys Cys
465                  470                  475                  480
Arg Pro Pro Arg Asp Arg Asn Gly Pro His Glu Arg Tyr His Leu Glu
           485                  490                  495
```

```
Val Glu Ala Gly Asn Thr Lys Val Arg Asn Glu Ser His Lys Asn Cys
            500                 505                 510

Asp Phe Arg Val Lys Asp Leu Gln Tyr Ser Thr Asp Tyr Thr Phe Lys
            515                 520                 525

Ala Tyr Phe His Asn Gly Asp Tyr Pro Gly Glu Pro Phe Ile Leu His
            530                 535                 540

His Ser Thr Ser Tyr Asn Ser Lys Ala
545                 550
```

(2) INFORMATION FOR SEQ ID NO:14:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:14:

```
Gln Gly His Leu Val His Met Thr Val Val Ser Gly Ser Asn Val Thr
1               5                   10                  15

Leu Asn Ile Ser Glu Ser Leu Pro Glu Asn Tyr Lys Gln Leu Thr Trp
            20                  25                  30

Phe Tyr Thr Phe Asp Gln Lys Ile Val Glu Trp Asp Ser Arg Lys Ser
            35                  40                  45

Lys Tyr Phe Glu Ser Lys Phe Lys Gly Arg Val Arg Leu Asp Pro Gln
50                  55                  60

Ser Gly Ala Leu Tyr Ile Ser Lys Val Gln Lys Glu Asp Asn Ser Thr
65                  70                  75                  80

Tyr Ile Met Arg Val Leu Lys Lys Thr Gly Asn Glu Gln Glu Trp Lys
            85                  90                  95

Ile Lys Leu Gln Val Leu Asp Pro Val Pro Lys Pro Val Ile Lys Ile
            100                 105                 110

Glu Lys Ile Glu Asp Met Asp Asp Asn Cys Tyr Leu Lys Leu Ser Cys
            115                 120                 125

Val Ile Pro Gly Glu Ser Val Asn Tyr Thr Trp Tyr Gly Asp Lys Arg
            130                 135                 140

Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
            165                 170                 175

Ser Ser Lys Asn Gly Thr Val Cys Leu Ser Pro Pro Cys Thr Leu Ala
            180                 185                 190

Arg Ser
```

(2) INFORMATION FOR SEQ ID NO:15:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:15:

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
```

-continued

```
              20                  25                  30
Gln Lys Glu Lys Lys Met Val Leu Thr Met Met Ser Gly Asp Met Asn
         35                  40                  45
Ile Trp Pro Glu Tyr Lys Asn Arg Thr Ile Phe Asp Ile Thr Asn Asn
 50                  55                  60
Lys Ser Ile Val Ile Leu Ala Leu Arg Pro Ser Asp Glu Gly Thr Tyr
 65                  70                  75                  80
Glu Cys Val Val Leu Lys Tyr Glu Lys Asp Ala Phe Lys Arg Glu His
                 85                  90                  95
Leu Ala Glu Val Thr Leu Ser Val Lys Ala Asp Phe Pro Thr Pro Ser
                100                 105                 110
Ile Ser Asp Phe Glu Ile Pro Thr Ser Asn Ile Arg Arg Ile Ile Cys
                115                 120                 125
Ser Thr Ser Gly Gly Phe Pro Glu Pro His Leu Ser Trp Leu Lys Arg
         130                 135                 140
Glu His Leu Ala Glu Val Ile Asn Thr Thr Val Ser Gln Asp Pro Glu
145                 150                 155                 160
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
                180                 185                 190
Gln Thr Phe Asn Trp Asn Thr Thr Lys Gln Glu His Phe Pro Asp Asn
         195                 200                 205
```

(2) INFORMATION FOR SEQ ID NO:16:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Ser Phe Leu Leu Phe Leu Thr Ile Ile Leu Leu Val Val Ile
 1               5                  10                  15
Gln Ile Gln Thr Gly Ser Leu Gly Gln Ala Thr Thr Ala Ala Ser Gly
                 20                  25                  30
Thr Asn Lys Asn Ser Thr Ser Thr Lys Lys Thr Pro Leu Lys Ser Gly
         35                  40                  45
Ala Ser Ser Ile Ile Asp Ala Gly Ala Cys Ser Phe Leu Phe Phe Ala
 50                  55                  60
Asn Thr Leu Met Cys Leu Phe Tyr Leu Ser
 65                  70
```

(2) INFORMATION FOR SEQ ID NO:17:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:17:

```
Asn Lys Val Val Leu Gly Lys Lys Gly Asp Thr Val Glu Leu Thr Cys
 1               5                  10                  15
Thr Ala Ser Gln Lys Lys Ser Ile Gln Phe His Trp Lys Asn Ser Asn
                 20                  25                  30
```

-continued

```
Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                 85                  90                  95

Val Phe Gly Leu Thr Ala Asn Ser Asp Thr His Leu Leu Gln Gly Gln
             100                 105                 110

Ser Leu Thr Leu Thr Leu Glu Ser Pro Pro Gly Ser Ser Pro Ser Val
             115                 120                 125

Gln Cys Arg Ser Pro Arg Gly Lys Asn Ile Gln Gly Gly Lys Thr Leu
             130                 135                 140

Ser Val Ser Gln Leu Glu Leu Gln Asp Ala Gly Thr Trp Ile Cys Thr
145                 150                 155                 160

Val Leu Gln Asn Gln Lys Lys Val Glu Phe Lys Ile Asp Ile Val Val
                 165                 170                 175

Leu Ala Glu Pro Arg Gly Pro Thr Ile Lys Pro Cys Pro Pro Cys Lys
             180                 185                 190

Cys Pro Ala Pro Asn Leu Leu Gly Gly Pro Ser Val Phe Ile Phe Pro
             195                 200                 205

Pro Lys Ile Lys Asp Val Leu Met Ile Ser Leu Ser Pro Ile Val Thr
             210                 215                 220

Cys Val Val Val Asp Val Ser Glu Asp Asp Pro Asp Val Gln Ile Ser
225                 230                 235                 240

Trp Phe Val Asn Asn Val Glu Val His Thr Ala Gln Thr Gln Thr His
                 245                 250                 255

Arg Glu Asp Tyr Asn Ser Arg Leu Arg Val Val Ser Ala Leu Pro Ile
             260                 265                 270

Gln His Gln Asp Trp Met Ser Gly Lys Glu Phe Lys Cys Lys Val Asn
             275                 280                 285

Asn Lys Asp Leu Pro Ala Pro Ile Glu Arg Thr Ile Ser Lys Pro Lys
             290                 295                 300

Gly Ser Val Arg Ala Pro Gln Val Tyr Val Leu Pro Pro Pro Glu Glu
305                 310                 315                 320

Met Thr Lys Lys Gln Val Thr Leu Thr Cys Met Val Thr Asp Phe Met
                 325                 330                 335

Pro Glu Asp Ile Tyr Val Glu Trp Thr Asn Asn Gly Lys Thr Glu Leu
             340                 345                 350

Asn Tyr Lys Asn Thr Glu Pro Val Leu Asp Ser Asp Gly Ser Tyr Phe
             355                 360                 365

Met Tyr Ser Lys Leu Arg Val Glu Lys Lys Asn Trp Val Glu Arg Asn
             370                 375                 380

Ser Tyr Ser Cys Ser Val Val His Glu Gly Leu His Asn His His Thr
385                 390                 395                 400

Thr Lys Ser Phe Ser Arg Thr Pro Gly Lys
                 405                 410
```

(2) INFORMATION FOR SEQ ID NO:18:

(i) SEQUENCE CHARACTERISTICS:
        (A) LENGTH: 418 amino acids
        (B) TYPE: amino acid (D) TOPOLOGY: linear (ii) MOLECULE TYPE: protein (xi) SEQUENCE DESCRIPTION: SEQ ID NO:18:

```
Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Ile Ala Gln Phe Arg
        35                  40                  45

Lys Glu Lys Glu Thr Phe Lys Glu Lys Asp Thr Tyr Lys Leu Phe Lys
        50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
                100                 105                 110

Trp Thr Cys Ile Asn Thr Thr Leu Thr Cys Glu Val Met Asn Gly Thr
            115                 120                 125

Asp Pro Glu Leu Asn Leu Tyr Gln Asp Gly Lys His Leu Lys Leu Ser
130                 135                 140

Gln Arg Val Ile Thr His Lys Trp Ile Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp Glu Pro Arg Gly Pro Thr Ile
            180                 185                 190

Lys Pro Cys Pro Pro Cys Lys Cys Pro Ala Pro Asn Leu Leu Gly Gly
        195                 200                 205

Pro Ser Val Phe Ile Phe Pro Pro Lys Ile Lys Asp Val Leu Met Ile
210                 215                 220

Ser Leu Ser Pro Ile Val Thr Cys Val Val Asp Val Ser Glu Asp
225                 230                 235                 240

Asp Pro Asp Val Gln Ile Ser Trp Phe Val Asn Asn Val Glu Val His
                245                 250                 255

Thr Ala Gln Thr Ala Thr His Arg Glu Asp Tyr Asn Ser Thr Leu Arg
            260                 265                 270

Val Val Ser Ala Leu Pro Ile Gln His Gln Asp Trp Met Ser Gly Lys
        275                 280                 285

Glu Phe Lys Cys Lys Val Asn Asn Lys Asp Leu Pro Ala Pro Ile Glu
        290                 295                 300

Glu Thr Ile Ser Lys Pro Lys Gly Ser Val Arg Ala Pro Gln Val Tyr
305                 310                 315                 320

Val Leu Pro Pro Pro Glu Glu Glu Met Thr Lys Lys Gln Val Thr Leu
                325                 330                 335

Thr Cys Met Val Thr Asp Phe Asn Pro Glu Asp Ile Tyr Val Glu Trp
            340                 345                 350

Thr Asn Asn Gly Lys Thr Glu Leu Asn Tyr Lys Asn Thr Glu Pro Val
        355                 360                 365

Leu Asp Ser Asp Gly Ser Tyr Phe Met Tyr Ser Lys Leu Arg Val Glu
370                 375                 380

Lys Lys Asn Trp Val Glu Arg Asn Ser Tyr Ser Cys Ser Val Val His
```

-continued

```
385                 390                 395                 400
Glu Gly Leu His Asn His His Thr Thr Lys Ser Phe Ser Arg Thr Pro
                    405                 410                 415
Gly Lys (2) INFORMATION FOR SEQ ID NO:19:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:19:

Asn Lys Ile Leu Val Lys Gln Ser Pro Met Leu Val Ala Tyr Asp Asn
 1               5                  10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
        50                  55                  60

Gly Phe Asn Cys Asp Gly Lys Leu Gly Asn Glu Ser Val Thr Phe Tyr
 65                 70                  75                  80

Leu Gln Asn Leu Tyr Tyr Asn Gln Thr Asp Ile Tyr Phe Cys Lys Ile
                85                  90                  95

Glu Tyr Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Glu Pro Arg Gly Pro Thr Ile Lys Pro Cys
130                 135                 140

Pro Pro Cys Lys Cys Pro Ala Pro Asn Leu Leu Gly Gly Pro Ser Val
145                 150                 155                 160

Phe Ile Phe Pro Pro Lys Ile Lys Asp Val Leu Met Ile Ser Leu Ser
                165                 170                 175

Pro Ile Val Thr Cys Val Val Asp Val Ser Glu Asp Asp Pro Asp
            180                 185                 190

Val Gln Ile Ser Trp Phe Val Asn Asn Val Glu Val His Thr Ala Gln
        195                 200                 205

Thr Gln Thr His Arg Glu Asp Tyr Asn Ser Thr Leu Arg Val Val Ser
210                 215                 220

Ala Leu Pro Ile Gln His Gln Asp Trp Met Ser Gly Lys Glu Phe Lys
225                 230                 235                 240

Cys Lys Val Asn Asn Lys Asp Leu Pro Ala Pro Ile Glu Arg Thr Ile
                245                 250                 255

Ser Lys Pro Lys Gly Ser Val Arg Ala Pro Gln Val Tyr Val Leu Pro
            260                 265                 270

Pro Pro Glu Glu Glu Met Thr Lys Lys Gln Val Thr Leu Thr Cys Met
        275                 280                 285

Val Thr Asp Phe Met Pro Glu Asp Ile Tyr Val Glu Trp Thr Asn Asn
290                 295                 300

Gly Lys Thr Glu Leu Asn Tyr Lys Asn Thr Glu Pro Val Leu Asp Ser
305                 310                 315                 320
```

-continued

```
Asp Gly Ser Tyr Phe Met Tyr Ser Lys Leu Arg Val Glu Lys Lys Asn
                325                 330                 335

Trp Val Glu Arg Asn Ser Tyr Ser Cys Ser Val Val His Glu Gly Leu
            340                 345                 350

His Asn His His Thr Thr Lys Ser Phe Ser Arg Thr Pro Gly Lys
        355                 360                 365

(2) INFORMATION FOR SEQ ID NO:20:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:20:

Met His Val Ala Gln Pro Ala Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Ala Gln Ile
            100                 105                 110

Tyr Val Ile Asp Pro Glu Pro Cys Pro Asp Ser Asp Glu Pro Arg Gly
        115                 120                 125

Pro Thr Ile Lys Pro Cys Pro Pro Cys Lys Cys Pro Ala Pro Asn Leu
    130                 135                 140

Leu Gly Gly Pro Ser Val Phe Ile Phe Pro Pro Lys Ile Lys Asp Val
145                 150                 155                 160

Leu Met Ile Ser Leu Ser Pro Ile Val Thr Cys Val Val Val Asp Val
                165                 170                 175

Ser Glu Asp Asp Leu Asp Val Gln Ile Ser Trp Phe Val Asn Asn Val
            180                 185                 190

Glu Val His Thr Ala Gln Thr Gln Thr His Arg Glu Asp Tyr Asn Ser
        195                 200                 205

Thr Leu Arg Val Val Ser Ala Leu Pro Ile Gln His Gln Asp Trp Met
    210                 215                 220

Ser Gly Lys Glu Phe Lys Cys Lys Val Asn Asn Lys Asp Leu Pro Ala
225                 230                 235                 240

Pro Ile Glu Arg Thr Ile Ser Lys Pro Lys Gly Ser Val Arg Ala Pro
                245                 250                 255

Gln Val Tyr Val Leu Pro Pro Glu Glu Glu Met Thr Lys Lys Gln
            260                 265                 270

Val Thr Leu Thr Cys Met Val Thr Asp Phe Met Pro Glu Asp Ile Tyr
        275                 280                 285

Val Glu Trp Thr Asn Asn Gly Lys Thr Glu Leu Asn Tyr Lys Asn Thr
    290                 295                 300

Glu Pro Val Leu Asp Ser Asp Gly Ser Tyr Phe Met Tyr Ser Lys Leu
```

```
305                 310                 315                 320
Arg Val Glu Lys Lys Asn Trp Val Glu Arg Asn Ser Tyr Ser Cys Ser
                325                 330                 335

Val Val His Glu Gly Leu His Asn His His Thr Thr Lys Ser Phe Ser
            340                 345                 350

Arg Thr Pro Gly Lys
            355

(2) INFORMATION FOR SEQ ID NO:21:

(i) SEQUENCE CHARACTERISTICS:
        (A) LENGTH: 378 amino acids
        (B) TYPE: amino acid
        (D) TOPOLOGY: linear (ii) MOLECULE TYPE: protein (xi) SEQUENCE DESCRIPTION: SEQ ID NO:21:

Pro Pro Glu Lys Lys Glu Leu Arg Lys Val Ala His Leu Thr Gly Lys
1               5                  10                  15

Ser Asn Ser Arg Ser Met Pro Leu Glu Trp Glu Asp Thr Tyr Gly Ile
            20                  25                  30

Val Leu Leu Ser Gly Val Lys Tyr Lys Gly Gly Leu Val Ile Asn
        35                  40                  45

Glu Thr Gly Leu Tyr Phe Val Tyr Ser Lys Val Tyr Phe Arg Gly Gln
50                  55                  60

Ser Cys Asn Asn Leu Pro Leu Ser His Lys Val Tyr Met Arg Asn Ser
65                  70                  75                  80

Lys Tyr Pro Gln Asp Leu Val Met Met Glu Gly Lys Met Met Ser Tyr
                85                  90                  95

Cys Thr Thr Gly Gln Met Trp Ala Arg Ser Ser Tyr Lys Gly Ala Val
            100                 105                 110

Phe Asn Leu Thr Ser Ala Asp His Leu Tyr Val Asn Val Ser Glu Leu
        115                 120                 125

Ser Leu Val Asn Phe Glu Glu Ser Gln Thr Phe Phe Gly Leu Tyr Lys
    130                 135                 140

Leu Glu Pro Arg Gly Pro Thr Ile Lys Pro Cys Pro Pro Cys Lys Cys
145                 150                 155                 160

Pro Ala Pro Asn Leu Leu Gly Gly Pro Ser Val Phe Ile Phe Pro Pro
                165                 170                 175

Lys Ile Lys Asp Val Leu Met Ile Ser Leu Ser Pro Ile Val Thr Cys
            180                 185                 190

Val Val Val Asp Val Ser Glu Asp Asp Pro Asp Val Gln Ile Ser Trp
        195                 200                 205

Phe Val Asn Asn Val Glu Val His Thr Ala Gln Thr Gln Thr His Arg
    210                 215                 220

Glu Asp Tyr Asn Ser Thr Leu Arg Val Val Ser Ala Leu Pro Ile Gln
225                 230                 235                 240

His Gln Asp Trp Met Ser Gly Lys Glu Phe Lys Cys Lys Val Asn Asn
                245                 250                 255

Lys Asp Leu Pro Ala Pro Ile Glu Arg Thr Ile Ser Lys Pro Lys Gly
            260                 265                 270

Ser Val Arg Ala Pro Gln Val Tyr Val Leu Pro Pro Glu Glu Glu
        275                 280                 285

Met Thr Lys Lys Gln Val Thr Leu Thr Cys Met Val Thr Asp Phe Met
    290                 295                 300
```

```
Pro Glu Asp Ile Tyr Val Glu Trp Thr Asn Asn Gly Lys Thr Glu Leu
305                 310                 315                 320

Asn Tyr Lys Asn Thr Glu Pro Val Leu Asp Ser Asp Gly Ser Tyr Phe
            325                 330                 335

Met Tyr Ser Lys Leu Arg Val Glu Lys Lys Asn Trp Val Glu Arg Asn
            340                 345                 350

Ser Tyr Ser Cys Ser Val Val His Glu Gly Leu His Asn His His Thr
            355                 360                 365

Thr Lys Ser Phe Ser Arg Thr Pro Gly Lys
            370                 375

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..33
        (D) OTHER INFORMATION: /label= primer (xi) SEQUENCE DESCRIPTION: SEQ ID NO:22:

CGCTCTAGAA TGAGCTTTCC ATGTAAATTT GTA                              33

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..36
        (D) OTHER INFORMATION: /label= primer (xi) SEQUENCE DESCRIPTION: SEQ ID NO:23:

TGTGGGCCCT CTGGGCTCGT CCAGACCTTT CTCTGG                           36

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..27
        (D) OTHER INFORMATION: /label= primer (xi) SEQUENCE DESCRIPTION: SEQ ID NO:24:

CGCTCTAGAA TGAACCGGGG AGTCCCT                                     27

(2) INFORMATION FOR SEQ ID NO:25:
```

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..34
            (D) OTHER INFORMATION: /label= primer (xi) SEQUENCE DESCRIPTION: SEQ ID NO:25:

GGGCCCTCTG GGCTCAGCTA GCACCACGAT GTCT                                34

(2) INFORMATION FOR SEQ ID NO:26:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..35
            (D) OTHER INFORMATION: /label= primer (xi) SEQUENCE DESCRIPTION: SEQ ID NO:26:

CCAGAGAAAG GTCTGGACGA GCCCAGAGGG CCCAC                               35

(2) INFORMATION FOR SEQ ID NO:27:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..34
            (D) OTHER INFORMATION: /label= primer (xi) SEQUENCE DESCRIPTION: SEQ ID NO:27:

AGACATCGTG GTGCTAGCTG AGCCCAGAGG GCCC                                34

(2) INFORMATION FOR SEQ ID NO:28:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..33
            (D) OTHER INFORMATION: /label= primer (xi) SEQUENCE DESCRIPTION: SEQ ID NO:28:

GGCGAATTCT TTACCCGGAG TCCGGGAGAA GCT                                 33

(2) INFORMATION FOR SEQ ID NO:29:

```
    (i) SEQUENCE CHARACTERISTICS:
         (A) LENGTH: 25 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..25
         (D) OTHER INFORMATION: /label= leader (xi) SEQUENCE DESCRIPTION: SEQ ID NO:29:

Met Asn Arg Gly Val Pro Phe Arg His Leu Leu Val Leu Gln Leu
1               5                   10                  15

Ala Leu Leu Pro Ala Ala Thr Gln Gly
            20                  25

(2) INFORMATION FOR SEQ ID NO:30:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..24
         (D) OTHER INFORMATION: /label= leader (xi) SEQUENCE DESCRIPTION: SEQ ID NO:30:

Met Ser Phe Pro Cys Lys Phe Val Ala Ser Phe Leu Leu Ile Phe Asn
1               5                   10                  15

Val Ser Ser Lys Gly Ala Val Ser
            20

(2) INFORMATION FOR SEQ ID NO:31:

(i) SEQUENCE CHARACTERISTICS:
         (A) LENGTH: 18 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..18
         (D) OTHER INFORMATION: /label= leader (xi) SEQUENCE DESCRIPTION: SEQ ID NO:31:

Met Leu Arg Leu Leu Leu Ala Leu Asn Leu Phe Pro Ser Ile Gln Val
1               5                   10                  15

Thr Gly (2) INFORMATION FOR SEQ ID NO:32:

(i) SEQUENCE CHARACTERISTICS:
         (A) LENGTH: 37 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..37
```

(D) OTHER INFORMATION: /label= leader (xi) SEQUENCE DESCRIPTION: SEQ ID NO:32:

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala
            35

(2) INFORMATION FOR SEQ ID NO:33:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..24
        (D) OTHER INFORMATION: /label= leader (xi) SEQUENCE DESCRIPTION: SEQ ID NO:33:

Met Pro Met Gly Ser Leu Gln Pro Leu Ala Thr Leu Tyr Leu Leu Gly
1               5                   10                  15

Met Leu Val Ala Ser Cys Leu Gly
            20

(2) INFORMATION FOR SEQ ID NO:34:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..25
        (D) OTHER INFORMATION: /label= leader (xi) SEQUENCE DESCRIPTION: SEQ ID NO:34:

Met Ala Gly Pro Pro Arg Leu Leu Leu Pro Leu Leu Leu Ala Leu
1               5                   10                  15

Ala Arg Gly Leu Pro Gly Ala Leu Ala
            20                  25

(2) INFORMATION FOR SEQ ID NO:35:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..26
        (D) OTHER INFORMATION: /label= leader (xi) SEQUENCE DESCRIPTION: SEQ ID NO:35:

Met Lys Asp Ser Cys Ile Thr Val Met Ala Met Ala Leu Leu Ser Gly
1               5                   10                  15

```
Phe Phe Phe Phe Phe Ala Pro Ala Ser Ser
            20                  25

(2) INFORMATION FOR SEQ ID NO:36:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /label= leader (xi) SEQUENCE DESCRIPTION: SEQ ID NO:36:

Met Leu Gly Leu Arg Pro Pro Leu Leu Ala Leu Val Gly Leu Leu Ser
1               5                   10                  15

Leu Gly Cys Val Leu Ser
            20

(2) INFORMATION FOR SEQ ID NO:37:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /label= leader (xi) SEQUENCE DESCRIPTION: SEQ ID NO:37:

Met Ala Arg Pro His Pro Trp Trp Leu Cys Val Leu Gly Thr Leu Val
1               5                   10                  15

Gly Leu Ser Ala
            20

(2) INFORMATION FOR SEQ ID NO:38:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /label= leader (xi) SEQUENCE DESCRIPTION: SEQ ID NO:38:

Met Ala Thr Leu Leu Leu Leu Leu Gly Val Leu Val Val Ser Pro
1               5                   10                  15

(2) INFORMATION FOR SEQ ID NO:39:

(i) SEQUENCE CHARACTERISTICS:
        (A) LENGTH: 23 amino acids
        (B) TYPE: amino acid
        (D) TOPOLOGY: linear (ii) MOLECULE TYPE: peptide
```

```
        (ix) FEATURE:
             (A) NAME/KEY: Peptide
             (B) LOCATION: 1..23
             (D) OTHER INFORMATION: /label= leader (xi) SEQUENCE DESCRIPTION: SEQ ID NO:39:

Met Tyr Leu Trp Leu Lys Leu Leu Ala Phe Gly Phe Ala Phe Leu Asp
1               5                  10                  15

Thr Glu Val Phe Val Thr Gly
            20

(2) INFORMATION FOR SEQ ID NO:40:

(i) SEQUENCE CHARACTERISTICS:
             (A) LENGTH: 26 amino acids
             (B) TYPE: amino acid
             (D) TOPOLOGY: linear (ii) MOLECULE TYPE: peptide (ix) FEATURE:
             (A) NAME/KEY: Peptide
             (B) LOCATION: 1..26
             (D) OTHER INFORMATION: /label= leader (xi) SEQUENCE DESCRIPTION: SEQ ID NO:40:

Met Trp Ser Arg Gly Trp Asp Ser Cys Leu Ala Leu Glu Leu Leu Leu
1               5                  10                  15

Leu Pro Leu Ser Leu Leu Val Thr Ser Ile
            20                  25

(2) INFORMATION FOR SEQ ID NO:41:

(i) SEQUENCE CHARACTERISTICS:
             (A) LENGTH: 34 amino acids
             (B) TYPE: amino acid
             (D) TOPOLOGY: linear (ii) MOLECULE TYPE: peptide (ix) FEATURE:
             (A) NAME/KEY: Peptide
             (B) LOCATION: 1..34
             (D) OTHER INFORMATION: /label= leader (xi) SEQUENCE DESCRIPTION: SEQ ID NO:41:

Met Gly His Thr Arg Arg Gln Gly Thr Ser Pro Ser Lys Cys Pro Tyr
1               5                  10                  15

Leu Asn Phe Phe Gln Leu Leu Val Leu Ala Gly Leu Ser His Phe Cys
            20                  25                  30

Ser Gly
```